United States Patent
Carreño Serraïma et al.

(10) Patent No.: US 9,464,129 B2
(45) Date of Patent: Oct. 11, 2016

(54) NEURONAL EXOCYTOSIS INHIBITING PEPTIDES

(75) Inventors: Cristina Carreño Serraïma, Gavá-Barcelona (ES); Berta Ponsati Obiols, San Quintí de Mediona-Barcelona (ES); Wim Van Den Nest, Gavá-Barcelona (ES); Jimena Fernandez Carneado, San Quintí de Mediona-Barcelona (ES); Antonio Ferrer Montiel, San Quintí de Mediona-Barcelona (ES); Juan Cebrian Puche, Gavá-Barcelona (ES); Nuria Almiñana Domenech, Gavá-Barcelona (ES)

(73) Assignee: BCN PEPTIDES S.A., San Quinti De Mediona, Barcelona (ES)

( * ) Notice: Subject to any disclaimer, the term of this patent is extended or adjusted under 35 U.S.C. 154(b) by 1802 days.

(21) Appl. No.: 12/447,136

(22) PCT Filed: Oct. 24, 2007

(86) PCT No.: PCT/ES2007/000603
§ 371 (c)(1),
(2), (4) Date: Sep. 16, 2009

(87) PCT Pub. No.: WO2008/049945
PCT Pub. Date: May 2, 2008

(65) Prior Publication Data
US 2010/0021510 A1 Jan. 28, 2010

(30) Foreign Application Priority Data
Oct. 25, 2006 (ES) .................. 200602720

(51) Int. Cl.
| | |
|---|---|
| A61K 38/00 | (2006.01) |
| C07K 14/705 | (2006.01) |
| A61K 8/14 | (2006.01) |
| A61K 8/64 | (2006.01) |
| A61Q 19/00 | (2006.01) |
| A61Q 19/10 | (2006.01) |
| A61Q 19/08 | (2006.01) |

(52) U.S. Cl.
CPC .............. *C07K 14/705* (2013.01); *A61K 8/14* (2013.01); *A61K 8/64* (2013.01); *A61Q 19/00* (2013.01); *A61Q 19/10* (2013.01); *A61K 38/00* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 7,015,192 B1 * | 3/2006 | Mira et al. ............. | 514/8.3 |
| 7,807,625 B2 * | 10/2010 | Majewski ............ | A61K 8/64 |
| | | | 424/401 |
| 2007/0166267 A1 * | 7/2007 | Majewski et al. ......... | 424/70.14 |

FOREIGN PATENT DOCUMENTS

EP    1180524 A1    2/2002

OTHER PUBLICATIONS

The International Search Report for the corresponding International Patent Application No. PCT/ES2007/000603, dated May 2, 2008. (14 pages).
Blanes-Mira, Clara, et al., "Small peptides patterned after the N-terminus domain in SNAP25 inhibit SNARE complex assembly and regulated exocytosis", *Journal of Neurochemistry*, vol. 88, 2004, pp. 124-135.
Chicarro, Christina, et al., "N-Terminal Fatty Acid Substitution Increases the Leishmanicidal Activity of CA(1-7) M(2-9), a Cecropin-Melittin Hybrid Peptide", *Antimicrobial Agents and Chemotherapy*, 2001, pp. 2441-2449.
Ferrer-Montiel, Antonio V., et al., "The 26-mer peptide released from SNAP-25 cleavage by botulinum neurotoxin E inhibits vesicle docking", *FEBS Letters*, vol. 435, 1998, pp. 84-88.
Gutierrez, Luis M., et al., "A peptide that mimics the carboxy-terminal domain of SNAP-25 blocks $Ca^{2+}$-dependent exocytosis in chromaffin cells", *FEBS Letters*, vol. 372, 372, 1995, pp. 39-43.
Tsutsui, Yasuo, et al., "Site-specific chemical modification with polyethylene glycol of recombinant immunotoxin anti-Tac(Fv)-PE38(LMB-2) improves antitumor activity and reduces animal toxicity and immunogenicity", *PNAS*, vol. 97, pp. 8548-8553.

* cited by examiner

*Primary Examiner* — Marcela M Cordero Garcia
(74) *Attorney, Agent, or Firm* — Lucas & Mercanti, LLP

(57) ABSTRACT

The invention relates to peptides of general formula (I):

$$R_1\text{-AA-}R_2 \qquad (I)$$

which can regulate neuronal exocytosis, their stereoisomers and racemic or non-racemic mixtures thereof, and the cosmetically or pharmaceutically acceptable salts thereof, wherein AA is a sequence of 3 to 40 adjacent amino acids contained in the amino acid sequence of the SNAP-25 protein, $R_1$ is selected from the group consisting of H or alkyl, aryl, aralkyl or acyl group; and $R_2$ is selected from the group consisting of amino, hydroxyl or thiol, substituted or non-substituted with aliphatic or cyclic groups, with the condition that when $R_1$ is H or acetyl, $R_2$ is not non-substituted amino, hydroxyl or thiol. The invention also relates to a method of obtaining such peptides, cosmetic or pharmaceutical compositions containing them and their use to treat those conditions requiring neuronal exocytosis regulation, preferably for treating the skin.

19 Claims, 1 Drawing Sheet

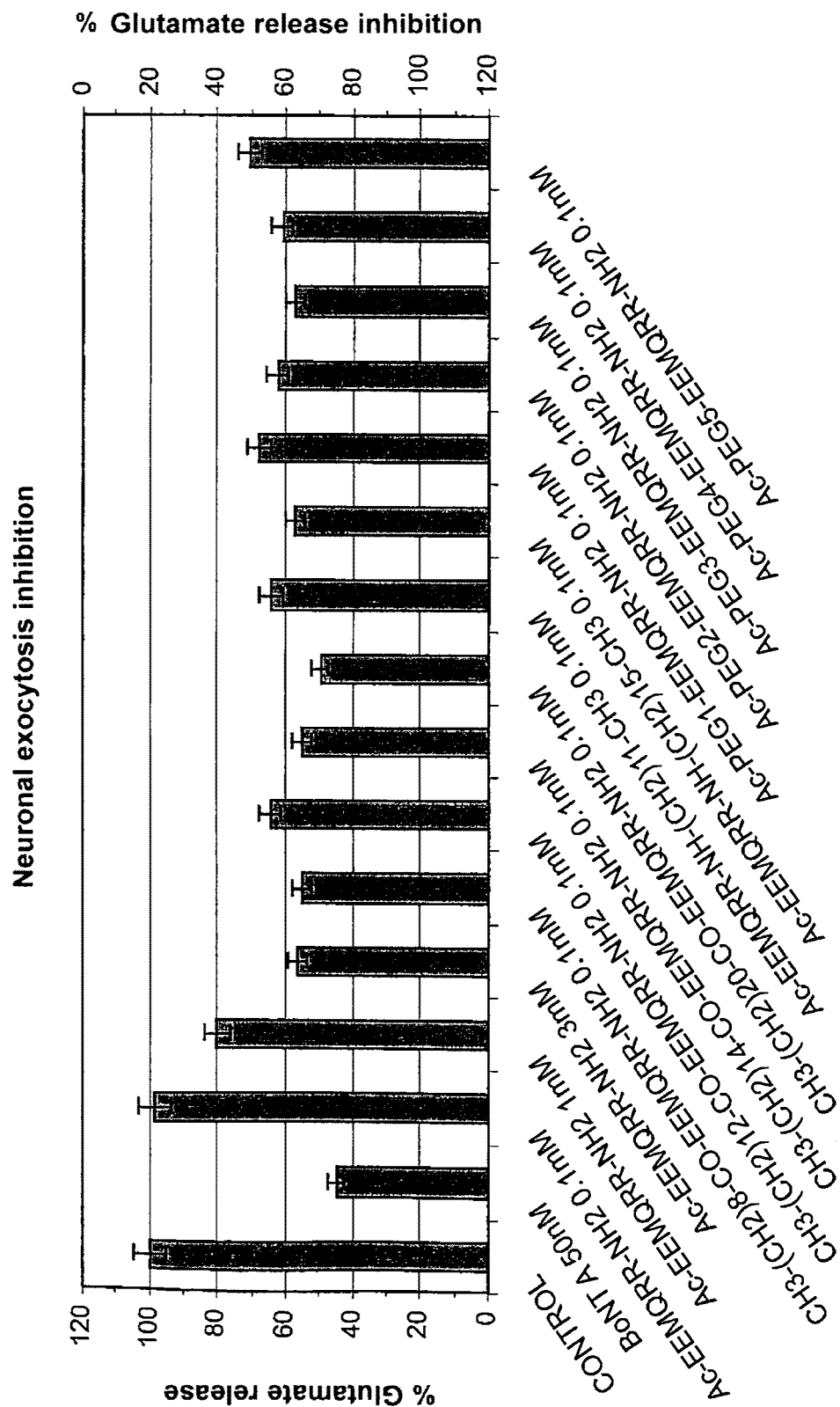

SEQUENCE LISTING

<160> NUMBER OF SEQ ID NOS: 32

<210> SEQ ID NO 1
<211> LENGTH: 206
<212> TYPE: PRT
<213> ORGANISM: Homo sapiens

<400> SEQUENCE: 1

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
        50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                 85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
            130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
            195                 200                 205

<210> SEQ ID NO 2
<211> LENGTH: 84
<212> TYPE: PRT
<213> ORGANISM: Homo sapiens

<400> SEQUENCE: 2

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe

<210> SEQ ID NO 3
<211> LENGTH: 37
<212> TYPE: PRT
<213> ORGANISM: Homo sapiens

<400> SEQUENCE: 3

Glu Ile Asp Thr Gln Asn Arg Gln Ile Asp Arg Ile Met Glu Lys Ala
1               5                   10                  15

Asp Ser Asn Lys Thr Arg Ile Asp Glu Ala Asn Gln Arg Ala Thr Lys
            20                  25                  30

Met Leu Gly Ser Gly
        35

<210> SEQ ID NO 4
<211> LENGTH: 13
<212> TYPE: PRT
<213> ORGANISM: Homo sapiens

<400> SEQUENCE: 4

Glu Leu Glu Glu Met Gln Arg Arg Ala Asp Gln Leu Ala
1               5                   10

```
<210> SEQ ID NO 5
<211> LENGTH: 16
<212> TYPE: PRT
<213> ORGANISM: Homo sapiens

<400> SEQUENCE: 5

Ser Leu Glu Ser Thr Arg Arg Met Leu Gln Leu Val Glu Glu Ser Lys
1               5                   10                  15

<210> SEQ ID NO 6
<211> LENGTH: 17
<212> TYPE: PRT
<213> ORGANISM: Homo sapiens

<400> SEQUENCE: 6

Asp Gln Ile Asn Lys Asp Met Lys Glu Ala Glu Lys Asn Leu Thr Asp
1               5                   10                  15

Leu

<210> SEQ ID NO 7
<211> LENGTH: 26
<212> TYPE: PRT
<213> ORGANISM: Homo sapiens

<400> SEQUENCE: 7

Ile Met Glu Lys Ala Asp Ser Asn Lys Thr Arg Ile Asp Glu Ala Asn
1               5                   10                  15

Gln Arg Ala Thr Lys Met Leu Gly Ser Gly
            20                  25

<210> SEQ ID NO 8
<211> LENGTH: 8
<212> TYPE: PRT
<213> ORGANISM: Homo sapiens

<400> SEQUENCE: 8

Glu Glu Met Gln Arg Arg Ala Asp
1               5

<210> SEQ ID NO 9
<211> LENGTH: 13
<212> TYPE: PRT
<213> ORGANISM: Homo sapiens

<400> SEQUENCE: 9

Leu Glu Ser Thr Arg Arg Met Leu Gln Leu Val Glu Glu
1               5                   10

<210> SEQ ID NO 10
<211> LENGTH: 12
<212> TYPE: PRT
<213> ORGANISM: Homo sapiens

<400> SEQUENCE: 10

Asn Lys Asp Met Lys Glu Ala Glu Lys Asn Leu Thr
1               5                   10

<210> SEQ ID NO 11
<211> LENGTH: 6
<212> TYPE: PRT
<213> ORGANISM: Homo sapiens

<400> SEQUENCE: 11
```

```
Glu Glu Met Gln Arg Arg
1               5

<210> SEQ ID NO 12
<211> LENGTH: 21
<212> TYPE: PRT
<213> ORGANISM: Homo sapiens

<400> SEQUENCE: 12

Met Ala Glu Asp Ala Asp Met Arg Asn Glu Leu Glu Glu Met Gln Arg
1               5                   10                  15

Arg Ala Asp Gln Leu
            20

<210> SEQ ID NO 13
<211> LENGTH: 23
<212> TYPE: PRT
<213> ORGANISM: Homo sapiens

<400> SEQUENCE: 13

Ala Asp Glu Ser Leu Glu Ser Thr Arg Arg Met Leu Gln Leu Val Glu
1               5                   10                  15

Glu Ser Lys Asp Ala Gly Ile
            20

<210> SEQ ID NO 14
<211> LENGTH: 12
<212> TYPE: PRT
<213> ORGANISM: Homo sapiens

<400> SEQUENCE: 14

Glu Leu Glu Glu Met Gln Arg Arg Ala Asp Gln Leu
1               5                   10

<210> SEQ ID NO 15
<211> LENGTH: 11
<212> TYPE: PRT
<213> ORGANISM: Homo sapiens

<400> SEQUENCE: 15

Glu Leu Glu Glu Met Gln Arg Arg Ala Asp Gln
1               5                   10

<210> SEQ ID NO 16
<211> LENGTH: 10
<212> TYPE: PRT
<213> ORGANISM: Homo sapiens

<400> SEQUENCE: 16

Glu Leu Glu Glu Met Gln Arg Arg Ala Asp
1               5                   10

<210> SEQ ID NO 17
<211> LENGTH: 9
<212> TYPE: PRT
<213> ORGANISM: Homo sapiens

<400> SEQUENCE: 17

Glu Leu Glu Glu Met Gln Arg Arg Ala
1               5

<210> SEQ ID NO 18
<211> LENGTH: 8
<212> TYPE: PRT
```

<213> ORGANISM: Homo sapiens

<400> SEQUENCE: 18

Glu Leu Glu Glu Met Gln Arg Arg
1               5

<210> SEQ ID NO 19
<211> LENGTH: 11
<212> TYPE: PRT
<213> ORGANISM: Homo sapiens

<400> SEQUENCE: 19

Leu Glu Glu Met Gln Arg Arg Ala Asp Gln Leu
1               5                   10

<210> SEQ ID NO 20
<211> LENGTH: 10
<212> TYPE: PRT
<213> ORGANISM: Homo sapiens

<400> SEQUENCE: 20

Leu Glu Glu Met Gln Arg Arg Ala Asp Gln
1               5                   10

<210> SEQ ID NO 21
<211> LENGTH: 9
<212> TYPE: PRT
<213> ORGANISM: Homo sapiens

<400> SEQUENCE: 21

Leu Glu Glu Met Gln Arg Arg Ala Asp
1               5

<210> SEQ ID NO 22
<211> LENGTH: 8
<212> TYPE: PRT
<213> ORGANISM: Homo sapiens

<400> SEQUENCE: 22

Leu Glu Glu Met Gln Arg Arg Ala
1               5

<210> SEQ ID NO 23
<211> LENGTH: 7
<212> TYPE: PRT
<213> ORGANISM: Homo sapiens

<400> SEQUENCE: 23

Leu Glu Glu Met Gln Arg Arg
1               5

<210> SEQ ID NO 24
<211> LENGTH: 10
<212> TYPE: PRT
<213> ORGANISM: Homo sapiens

<400> SEQUENCE: 24

Glu Glu Met Gln Arg Arg Ala Asp Gln Leu
1               5                   10

<210> SEQ ID NO 25
<211> LENGTH: 9
<212> TYPE: PRT
<213> ORGANISM: Homo sapiens

```
<400> SEQUENCE: 25

Glu Glu Met Gln Arg Arg Ala Asp Gln
1               5

<210> SEQ ID NO 26
<211> LENGTH: 7
<212> TYPE: PRT
<213> ORGANISM: Homo sapiens

<400> SEQUENCE: 26

Glu Glu Met Gln Arg Arg Ala
1               5

<210> SEQ ID NO 27
<211> LENGTH: 6
<212> TYPE: PRT
<213> ORGANISM: Homo sapiens

<400> SEQUENCE: 27

Lys Asn Leu Thr Asp Leu
1               5

<210> SEQ ID NO 28
<211> LENGTH: 20
<212> TYPE: PRT
<213> ORGANISM: Homo sapiens

<400> SEQUENCE: 28

Ser Asn Lys Thr Arg Ile Asp Glu Ala Asn Gln Arg Ala Thr Lys Met
1               5                   10                  15

Leu Gly Ser Gly
            20

<210> SEQ ID NO 29
<211> LENGTH: 17
<212> TYPE: PRT
<213> ORGANISM: Homo sapiens

<400> SEQUENCE: 29

Thr Arg Ile Asp Glu Ala Asn Gln Arg Ala Thr Lys Met Leu Gly Ser
1               5                   10                  15

Gly

<210> SEQ ID NO 30
<211> LENGTH: 14
<212> TYPE: PRT
<213> ORGANISM: Homo sapiens

<400> SEQUENCE: 30

Asp Glu Ala Asn Gln Arg Ala Thr Lys Met Leu Gly Ser Gly
1               5                   10

<210> SEQ ID NO 31
<211> LENGTH: 11
<212> TYPE: PRT
<213> ORGANISM: Homo sapiens

<400> SEQUENCE: 31

Asn Gln Arg Ala Thr Lys Met Leu Gly Ser Gly
1               5                   10

<210> SEQ ID NO 32
<211> LENGTH: 10
```

```
<212> TYPE: PRT
<213> ORGANISM: Homo sapiens

<400> SEQUENCE: 32

Gln Arg Ala Thr Lys Met Leu Gly Ser Gly
1               5                   10
```

NEURONAL EXOCYTOSIS INHIBITING PEPTIDES

FIELD OF THE INVENTION

The present invention relates to peptides which can regulate neuronal exocytosis and to cosmetic or pharmaceutical compositions containing said peptides useful in the treatment of the conditions requiring neuronal exocytosis regulation, such as for example muscle spasticity, facial asymmetry and/or facial wrinkles, preferably expression wrinkles.

BACKGROUND OF THE INVENTION

One of the most visible signs of human aging are the changes experienced by the skin: dryness, appearance of spots, flaccidity and wrinkles. These effects can be caused by external agents such the constant exposure to the sun, atmospheric pollution or contact with chemical agents present in cleaning products for example, but are also the result of intrinsic physiological, biochemical and histological changes of the human organism, due to the decrease of the synthesis of proteins such as collagen or elastin, to an increase of proteolysis, and to a general breaking of the skin barrier, of the connective tissue and of cohesion.

Different active ingredients have been described for preventing and decreasing aging symptoms, such as retinoids, hydroxy acids, flavonoids or vitamin C and E derivatives, for example. Said compounds normally act by improving skin hydration, increasing cell renovation or preventing the degeneration of the tissue forming the skin; however, their efficacy in preventing and treating facial wrinkles caused by muscle contraction is limited. The facial expression wrinkle formation basis or mechanism is a tension of epidermal muscles dragging the skin inwardly. This muscular tension is the result of a hyperactivity of the nerves enervating facial muscles. Nervous hyperactivity is characterized by an uncontrolled and excessive release of neurotransmitters exciting muscular fibers. To that end, molecules regulating neuronal exocytosis contribute to relaxing muscular tension and subsequently, to eliminating facial wrinkles.

There is therefore a need to develop new active ingredients with proven efficacy for the preparation of a cosmetic or pharmaceutical composition for regulating neuronal exocytosis and, therefore for treating muscle spasticity and reducing and/or eliminating facial asymmetry and/or facial wrinkles, especially expression wrinkles.

Expression wrinkles are the wrinkles resulting from the stress exerted by the contractions of facial muscles responsible for causing facial expressions on the skin of the face. Expression wrinkles are usually located on the forehead, in the space between the eyebrows, around the mouth and/or around the eyes. Depending on the shape of the face, the expression frequency and the existence of tics (convulsive movements which are frequently repeated, caused by the involuntary contraction of one or several muscles, in this case facial muscles), expression wrinkles may even appear during adolescence. External factors such as exposure to the sun emphasize their depth and visibility.

Botulinum toxins have been widely used with the aim of reducing and/or eliminating expression wrinkles, especially serotype A (BOTOX® Cosmetic, Allergan Inc.) [Carruthers J. D. and Carruthers J. A. (1992) "*Treatment of glabellar frown lines with C. botulinum-A exotoxin*" *J. Dermatol. Surg. Oncol.* 18, 17-21; Mendez-Eastman S. K. (2003) "*Botox: a review*" *Plast. Surg. Nurs.* 23, 64-69]. The therapeutic and cosmetic treatment with BOTOX® consists of the localized injection of diluted pharmaceutical preparations (botulinum A-hemagglutinin complex, 500 kDa) in the areas in which the muscular tension is located. The paralytic effects of the toxin are reversible with an average duration of 6 months [Jankovic J. and Brin F. M. (1991) "*Therapeutic uses of botulinum toxin*" *New Engl. J. Med.* 324, 1186-1194; Jankovic J. (1994) "*Botulinum toxin in movement disorders*" *Curr. Opin. Neurol.* 6, 358-366]. The treatment therefore requires the repeared injection of botulinum toxin. The main problem of this treatment is the possibility of triggering an immune reaction against the pharmaceutical preparation due to the fact that its molecular size can be recognized by the patient's immune system. The appearance of antibodies against the botulinum toxin is a serious problem because it contributes to a clear loss of treatment efficacy [Jankovic J. and Brin F. M. (1991) "*Therapeutic uses of botulinum toxin*" *New Engl. J. Med.* 324, 1186-1194; Jankovic J. (1994) "*Botulinum toxin in movement disorders*" *Curr. Opin. Neurol.* 6, 358-366; Jankovic J. and Brin M. F. (1997) "*Botulinum toxin: historical perspective and potential new indications*" *Muscle Nerve Suppl.* 6, S129-5145; Davis L. E. (1993) "*Botulinum toxin-from poison to medicine*" *West J. Med.* 128, 25-28; Hughes A. J. (1994) "*Botulinum toxin in clinical practise*" *Drugs* 48, 888-893; Hambleton P. (1992) "*Clostridium botulinum toxins a general review of involvement in disease, structure, mode of action and preparation for clinical use*" *J. Neurol.* 239, 16-20; Borodic G. E. and Pearces L. B. (1994) "*New concepts in botulinum toxin therapy*" *Drug Safety* 11, 145-152; Brin M. F., Blitzer A., Stewart C., Pine Z., Borg-Stein J., Miller J., Nagalapura N. S. and Rosenfeld D. B. (1993) "*Disorders with excessive muscle contraction: Candidates for treatment with intramuscular botulinum toxin* (BoTox®)" *Botulinum and Tetanus Neurotoxins* (Ed. B. R. DasGupata), 559-576]. This loss of treatment efficacy with BOTOX® entails the need to increase the concentration of the preparation in subsequent treatments, which in turn causes a potentiation of the immune response. As an alternative to the treatment with botulinum toxin serotype A, the use of different serotypes of botulinum toxins, such as BoTox B, BoTox F and BoTox E, has been considered. Nevertheless, the application of pharmaceutical applications with different serotypes cannot be considered a solution to the problem, because sooner or later, the immune reaction can occur again. Furthermore, the treatment with botulinum toxins is expensive, mainly due to the lability and instability of the pharmaceutical preparations containing them.

There is therefore a pressing need to develop molecules imitating the paralytic effects of botulinum toxins but that are provided with much simpler and stabler molecular structures which do not induce immune reactions and the production cost of which is cost-effective. Molecules with a peptide nature comply with these properties.

At a molecular level, botulinum toxins are proteases degrading neuronal proteins that are involved in the calcium ion-activated exocytosis mechanism [Schiavo G., Rossetto O. and Montecucco C. (1996) "*Bases Moleculares del tétanos y del botulismo*" *Investigación y Ciencia* 234, 46-55; Montecucco C. and Schiavo G. (1994) "*Mechanism of action of tetanus and botulinum neurotoxins*" *Mol. Microbiol.* 13, 1-8; Schiavo G., Rosetto O., Benfenati F., Poulain B. and Montecucco, C. (1994) "*Tetanus and botulinum neurotoxins are zinc proteases specific for components of the neuroexocytosis apparatus*" *Ann. NY Acad. Sci.* 710, 65-75]. For example, botulinum toxin A, the most commonly used in clinical practice and cosmetics due to its applications in the elimination of facial wrinkles and facial asymmetry, and to ease the symptomatology of spasmodic diseases, truncates the neuronal SNAP-25 protein. This SNAP-25 protein has an important role in neurosecretion because it is involved in the formation of a protein complex (known as SNARE or fusion complex) directing and controlling the release of acetylcholine accumulated in vesicles. The core of said fusion complex is formed by syntaxin and SNAP-25 proteins, located in the presynaptic plasma membrane, and the synaptobrevin or VAMP protein, located in the vesicular plasma membrane [Calakos N. and Scheller R. H. (1996) "*Synaptic vesicle biogenesis, docking and fusion: a molecular description*" Physiol. Rev. 76, 1-29; Sutton R. B., Fasshauer D., Jahn R. and Brunger A. T. (1998) "*Crystal structure of a SNARE complex involved in synaptic exocytosis at 2.4Å resolution*" Nature 395, 347-3531 The main function of the fusion complex is to move the vesicle loaded with neurotransmitter (acetylcholine) closer to and place it in contact with the presynaptic plasma membrane [Calakos N. and Scheller R. H. (1996) "*Synaptic vesicle biogenesis, docking and fusion: a molecular description*" Physiol. Rev. 76, 1-29; Sutton R. B., Fasshauer D., Jahn R. and Brunger A. T. (1998) "*Crystal structure of a SNARE complex involved in synaptic exocytosis at 2.4Å resolution*" Nature 395, 347-353]. The fusion of both plasma membranes in response to a calcium concentration elevation is thus favored, thus causing the release of the neurotransmitter. Said vesicular fusion and anchoring SNARE protein complex therefore forms a key target for controlling neurosecretion. The truncation of any of the proteins forming the fusion complex prevents its assembly and therefore inhibits vesicular release and regulates neuronal exocytosis.

It is known in the state of the art that certain peptides derived from the sequences of the proteins forming the SNARE complex can inhibit neuronal exocytosis, such as for example peptides derived from the amino and carboxyl domains of the SNAP-25 protein [Apland J. P., Biser J. A., Adler M., Ferrer-Montiel A. V., Montal M., Canaves J. M. and Filbert, M. G. (1999) "*Peptides that mimic the carboxy-terminal domain of SNAP-25 block acetylcholine release at an aplysia synapse*" J. Appl. Toxicol. 19, Suppl. 1: S23-S26; Mehta P. P., Batternger E. and Wilson M. (1996) "*SNAP-25 and synaptotagmin involvement in the final $Ca^{2+}$-dependent triggering of neurotransmitter exocytosis*" Proc. Natl. Acad. Sci. USA 93, 10471-10476; Ferrer-Montiel A. V., Gutierrez L. M., Apland J. P., Canaves J. M., Gil A., Viniegra S., Biser J. A., Adler M. and Montal M. (1998) "*The 26-mer peptide released from cleavage by botulinum neurotoxin E inhibits vesicle docking*" FEBS Lett. 435, 84-88; Gutierrez L. M., Canaves J. M., Ferrer-Montiel A. V., Reig J. A., Montal M. and Viniegra S. (1995) "*A peptide that mimics the carboxy-terminal domain of SNAP-25 blocks $Ca^{2+}$-dependent exocytosis in chromaffin cells*" FEBS Lett. 372, 39-43; Gutierrez L. M., Viniegra S., Rueda J., Ferrer-Montiel A. V., Canaves J. M. and Montal M. (1997) "*A peptide that mimics the C-terminal sequence of SNAP-25 inhibits secretory vesicle docking in chromaffin cells*" J. Biol. Chem. 272, 2634-2639; Blanes-Mira C, Valera E., Fernández-Ballester G., Merino J. M., Viniegra S., Gutierrez L. M., Perez-Payá E. and Ferrer-Montiel A. (2004) "*Small peptides patterned after the N-terminus domain of SNAP-25 inhibit SNARE complex assembly and regulated exocytosis*" J. Neurochem. 88, 124-135], the peptides derived from the amino acid sequence of syntaxin [Martin F., Salinas E., Vazquez J., Soria B. and Reig J. A. (1996) "*Inhibition of insulin release by synthetic peptides show that the H3 region at the C-terminal domain of syntaxin-1 is crucial for $Ca^{2+}$-but not for guanosine 5'-[gamma-thio]thriphosphate-induced secretion*" Biochem. J. 320, 201-2051, of the sinaptobrevina [Cornille F., Deloye F., Fournie-Zaluski M. C., Rogues B. P. and Poulain B. (1995) "*Inhibition of neurotransmitter release by synthetic proline-rich peptides shows that the N-terminal domain of vesicle-associated membrane protein/synaptobrevin is critical for neuro-exocytosis*" J. Biol. Chem. 270, 16826-16830], of synaptotagmin [Mehta P. P., Batternger E. and Wilson M. (1996) "*SNAP-25 and synaptotagmin involvement in the final $Ca^{2+}$-dependent triggering of neurotransmitter exocytosis*" Proc. Natl. Acad. Sci. USA 93, 10471-10476] and of the snapin protein [Ilardi J. M., Mochida S. and Sheng Z. H. (1999) "*Snapin: A SNARE associated protein implicated in synaptic transmission*" Nat. Neurosci. 2, 119-124]. In the same way, synthectic peptides obtained by rational design or by tracing synthetic chemical libraries which can interfere in the formation of the SNARE complex, inhibiting neuronal exocytosis, have also been described [Blanes-Mira C., Pastor M. T., Valera E., Fernández-Ballester G., Merino J. M., Gutierrez L. M., Perez-Paya E. and Ferrer-Montiel A. (2003) "*Identification of SNARE complex modulators that inhibit exocytosis form an α-helix-constrained combinatorial library*" Biochem J. 375, 159-166].

The industrial application of this type of compounds has been limited. The cosmetic industry has carried out considerable efforts to develop compounds imitating the action of botulinum toxins with exclusive use in treating and preventing the formation of expression wrinkles [Blanes-Mira C., Clemente J., Jodas G., Gil A., Fernández-Ballester G., Ponsati B., Gutierrez L. M., Pérez-Payá E. and Ferrer-Montiel, A. (2002) "*A synthetic hexapeptide (Argireline®) with anti-wrinkle activity*" Int. J. Cosmetic Res. 24, 303-310]. Specifically, patent EP1,180,524 of Lipotec, S. A. describes peptides derived from the amino-terminal fragment of the SNAP-25 protein having an anti-wrinkle effect, and international patent application WO97/34620 also describes peptides derived from the amino acid sequence of the SNAP-25 protein, specifically from its carboxy-terminal region, or from synaptobrevin or from syntaxin which can inhibit neuronal exocytosis.

None of the patents described above relates to irreversibly chemically modified derivatives of the SNAP-25 protein as regulating agents of neuronal exocytosis. Patent EP1,180,524 describes potential reversible chemical modifications of the peptides of the amino-terminal end of the SNAP-25 protein for the purpose of increasing its bioavailability and its ease in passing through the blood-brain barrier and epithelial tissue, such as the esterification of the side chains of aspartic and glutamic residues, which will subsequently be degraded in vivo by intracellular esterases, recovering the unmodified peptide responsible for biological activity. Surprisingly, the applicant of the present invention has discovered that chemically irreversible modifications of the amino and carboxyl ends of said peptides not only provide them with greater resistance to degradation against intracellular proteases, causing a longer duration of their effect as neuronal exocytosis regulators, but surprisingly, they can increase their in vitro efficacy from two to thirty times with respect to that of the corresponding unmodified peptide.

The modification of proteins with lipid chains is described as an irreversible modification when it is carried out on amino groups present in their sequences, either in their amino-terminal end or in side chains of lysine residues, whereas it is considered reversible when it is carried out on the thiol groups of cysteine residues, because the modified peptide or protein are hydrolyzed in vivo by the corresponding thioesterases [Magee A. I. (1990) "*Lipid modification of* proteins and its relevance to protein targeting" *J. Cell Sci.* 97, 581-584; Mumby S. M. (1997) *"Reversible palmitoylation of signaling proteins" Curr. Opin. Cell Biol.* 9, 148-154]. The state of the art describes examples of irreversible modifications of peptides with fatty acid chain derivatives for the purpose of improving their in vivo efficacy, increasing their permeation through the skin [Lintner K. and Peschard O. (2000) *"Biologically active peptides: from a laboratory bench curiosity to a functional skin care product" Int. J. Cosmet. Sci.* 22, 207-218] or achieving a better immunological response for their development as potential vaccines [Gahery H., Choppin J., Bourgault I., Fischer E., Maillere B. and Guillet J. G. (2005) *"HIV preventive vaccine research at the ANRS: the lipopeptide vaccine approach" Therapie* 60, 243-248], as well as for inducing a greater cytotoxic effect on bacteria [Eisenstein B. I. (2004) *"Lipopeptides, focusing on daptomycin, for the treatment of Gram-positive infections" Expert Opin. Investig. Drugs* 13, 1159-1169] or on fungi [Avrahami D. and Shai Y. (2004) *"A New Group of Antifungal and Antibacterial Lipopeptides Derived from Non-membrane Active Peptides Conjugated to Palmitic Acid" J. Biol. Chem.* 279, 12277-12285]. This type of modifications does not always cause a change in the in vitro efficacy of said peptides; for example the palmitoylation of the GHK tripeptide does not modify its capacity to induce collagen synthesis in fibroblasts [Lintner K. and Peschard O. (2000) *"Biologically active peptides: from a laboratory bench curiosity to a functional skin care product" Int. J. Cosmet. Sci.* 22, 207-218], so a person skilled in the art at the time of the present invention could not predict if the modification of a peptide with a hydrocarbon group would increase, decrease or leave its in vitro efficacy unaltered with respect to the corresponding unmodified peptide.

The irreversible chemical modification of peptides and proteins by means of the covalent incorporation of repetitive polyethylene glycol units, known as "PEGylation", basically for the purpose of increasing the half-life period in vivo, decreasing the toxicity and reducing the imunogenicity and antigenicity of peptides and proteins, is also known in the state of the art [Savoca K. V., Abuchowski A., van Es T., Davis F. F. and Palczuk N. C. (1979) *"Preparation of a non-immunogenic arginase by the covalent attachment of polyethylene glycol" Biochim. Biophys. Acta* 578, 47-53; Hershfield M. S., Buckley R. H., Greenberg M. L., Melton A. L., Schiff R., Hatem C., Kurtzberg J., Marked M. L., Kobayashi R. H., Kobayashi A. L., et al. (1987) *"Treatment of adenosine deaminase deficiency with polyethylene glycol-modified adenosine deaminase" N. Engl. J. Med.* 316, 589-596; Katre N. V. (1990) *"Immunogenicity of recombinant IL-2 modified by covalent attachment of polyethylene glycol" J. Immunol.* 144, 209-213; Wang Q. C., Pai L. H., Debinski W., FitzGerald D. J. and Pastan I. (1993) *"Polyethylene glycol-modified chimeric toxin composed of transforming growth factor oc and Pseudomonas exotoxin" Cancer Res.* 53, 4588-4594; Clark R., Olson K., Fuh G., Marian M., Mortensen D., Teshima G., Chang S., Chu H., Mukku V., Canova-Davis E., Somers T., Cronin M., Winkler M. and Wells J. A. (1996) *"Long-acting growth hormones produced by conjugation with polyethylene glycol" J. Biol. Chem.* 271, 21969-21977; He X. H., Shaw P. C. and Tam S. C. (1999) *"Reducing the immunogenicity and improving the in vivo activity of trichosanthin by site-directed pegylation" Life Sci.* 65, 355-368; Harris J. M. and Chess R. B. (2003) *"Effect of PEGylation on pharmaceuticals" Nat. Rev. Drug Discov.* 2, 214-221]. The examples existing in the state of the art describes modifications of peptides and proteins for the purpose of improving their pharmacological properties of distribution and elimination and thus improving their in vivo biological activity without altering their in vitro biological activity, but in no case do they suggest that the potential PEGylation can increase the in vitro biological activity of the protein, rather on the contrary, there are described examples such as the case of PEGylated interferon in which the in vitro activity is reduced, comparing it with that of the native interferon [Rajender Reddy K., Modi M. W. and Pedder S. (1992) *"Use of peginterferon alfa-2a (40 KD) (Pegasys) for the treatment of hepatitis C" Adv. Drug Deliv. Rev.* 54(4), 571-86].

Surprisingly, the present invention shows that the irreversible chemical modification of peptide sequences derived from the SNAP-25 protein can increase the efficacy of said sequences in neuronal exocytosis inhibition. There is no indication in the state of the art that said modifications must increase the inhibitory effect of said peptides, therefore a person skilled in the art could not deduce the nature of the required modifications of the peptides to increase their capacity to inhibit neuronal exocytosis.

The present invention thus provides a novel solution to the existing needs, comprising the discovery of irreversibly chemically modified peptide sequences derived from the SNAP-25 protein that can inhibit neuronal exocytosis in a more effective and prolonged manner than the corresponding unmodified peptides that are already known in the state of the art.

DESCRIPTION OF THE INVENTION

The present invention provides a simple, effective and risk-free solution for regulating neuronal exocytosis, comprising the application in the body of a mammal of a composition containing at least one peptide having an amino acid sequence derived from the amino acid sequence of the SNAP-25 protein and which is irreversibly chemically modified in its amino and/or carboxyl ends.

Therefore, a first aspect of the invention relates to a peptide which can regulate neuronal exocytosis, according to general formula (I):

$$R_1\text{-AA-}R_2 \tag{I}$$

its stereoisomers and racemic or non-racemic mixtures thereof, and the cosmetically or pharmaceutically acceptable salts thereof, wherein AA is a sequence of 3 to 40 adjacent amino acids contained in the amino acid sequence SEQ ID No. 1;

$R_1$ is selected from the group consisting of H or alkyl, aryl, aralkyl or acyl group;

and $R_2$ is selected from the group consisting of amino, hydroxyl or thiol, substituted or non-substituted with aliphatic or cyclic groups;

with the condition that when $R_1$ is H or acetyl, $R_2$ is not non-substituted amino, hydroxyl or thiol.

The preferred structures of the peptides shown in general formula (I) are those wherein $R_1$ is H or acetyl or a saturated or unsaturated, linear, branched or cyclic $C_3$ to $C_{24}$ acyl group or a polyethylene glycol polymer;

$R_2$ is amino or hydroxyl optionally substituted with saturated or unsaturated, linear, branched or cyclic $C_1$ to $C_{24}$ aliphatic groups;

with the condition that when $R_1$ is H or acetyl, $R_2$ is not non-substituted amino or hydroxyl.

More preferred structures are those in which the polyethylene glycol polymer is

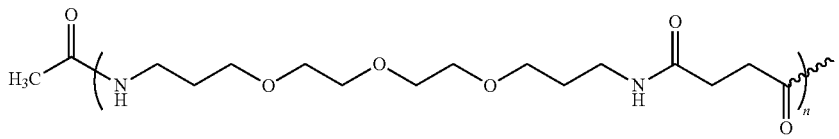

wherein n can vary from 1 to 100, and more preferably it can vary between 1 and 5.

Additionally, preferred structures are those wherein $R_1$ is an acyl group of formula $CH_3—(CH_2)_m—CO—$, wherein m can vary between 1 and 22.

The peptides of the present invention can exist as stereoisomers or mixtures of stereoisomers; for example, the amino acids forming them can have an L-, D-configuration, or can be racemic independently from one another. It is therefore possible to obtain isomeric mixtures as well as racemates or diastereoisomeric mixtures, or pure diastereoisomers or enantiomers, depending on the number of asymmetric carbons and on which isomers or isomeric mixtures are present. The preferred structures of the peptides of the invention are pure isomers, i.e., enantiomers or diastereoisomers.

Within the context of the present invention, the term "aliphatic group" relates to a saturated or unsaturated, linear or cyclic group.

The term "hydrocarbon group" is used in the present invention to cover alkyl, alkenyl or alkynyl groups for example.

The term "alky group" relates to a saturated, linear or branched hydrocarbon group, including, for example, methyl, ethyl, isopropyl, isobutyl, t-butyl, heptyl, dodecyl, hexadecyl, octadecyl, amyl, 2-ethylhexyl, 2-methylbutyl, 5-methylhexyl and the like.

The term "alkenyl group" relates to an unsaturated, linear or branched hydrocarbon group with one or more carbon-carbon double bonds, such as vinyl group.

The term "alkynyl group" relates to an unsaturated, linear or branched hydrocarbon group with one or more carbon-carbon triple bonds.

The term "cyclic group" relates to a closed hydrocarbon ring, which can be classified as an alicyclic, aromatic or heterocyclic group.

The term "alicyclic group" relates to a cyclic hydrocarbon group with properties similar to aliphatic groups.

The term "aromatic group" or "aryl group" relates to a mono- or polycyclic aromatic hydrocarbon group.

The term "heterocyclic group" relates to a closed hydrocarbon ring, in which one or more than one of the atoms of the ring is an element other than carbon (for example, nitrogen, oxygen, sulfur, etc.).

The term "polyethylene glycol polymer" relates to substituted or non-substituted hydrocarbon chains containing repetitive units of the $—CH_2CH_2O—$ group.

As understood in this technical area, the existence of a high degree of substitution is not only tolerated but recommended. Therefore, there may be substitution in the peptides of the present invention. For the purpose of simplifying the present description of the invention, the terms "group" and "block" will be used to distinguish between chemical species allowing substitution or which can be substituted ("group"), and those which do not allow substitution or which cannot be substituted ("block"). In this way, when the term "group" is used to describe a chemical substituent, the described chemical material includes both the non-substituted group and that containing the O, N or S atoms.

On the other hand, when the term "block" is used to describe a chemical compound or substituent, only non-substituted chemical material can be included. For example, the expression "alkyl group" will not only include open-chain saturated alkyl compounds, such as methyl, ethyl, propyl, isobutyl and the like, but also alkyl substituents containing other substituents known in the state of the art, such as hydroxyl, alkoxyl, amino, carboxyl, carboxamide, halogen atoms, cyano, nitro, alkylsulfonyl, and others. In this way, "alkyl group" includes ether, haloalkyl, alcohol, thiol, carboxyl, amine, hydroxyalkyl, sulfoalkyl, guanidine groups and others. On the other hand, the expression "alkyl block" is only limited to the inclusion of open-chain saturated alkyl substituents, such as methyl, ethyl, propyl, isobutyl and the like.

In the context of the present invention "amino acid sequence derived from the amino acid sequence of the SNAP-25 protein" means any amino acid sequence or fragment contained in the amino acid sequence of the SNAP-25 protein, defined by the SEQ ID No.1, or any amino acid sequence differing from a sequence contained in the sequence SEQ ID No.1 by mutation, insertion, deletion or substitution of at least one amino acid, or by genetic code degeneracy, provided that it corresponds to a peptide having SNAP-25 protein activity. The mutations, insertions or substitutions can take place by means of genetically encoded amino acids or by means of non-encoded amino acids, either natural or synthetic, such as for example and in a non-limiting sense, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statin, β-alanin, norleucine, N-methylamino acids, β-amino acids or γ-amino acids among others, as well as their derivatives. A list of synthetic amino acids can be found in the article "Unusual amino acids in peptide synthesis" by Roberts D. C. and Vellaccio F., in The Peptides, Vol. 5 (1983), Chapter VI, Gross E. and Meienhofer J., Eds., Academic Press, New York, USA, or in commercial catalogs of the specialized companies in the sector, such as for example NeoMPS, Bachem, Novabiochem, Sigma-Aldrich, Peptides International, Advanced ChemTech, Chem-Impex, Maybridge Chemical, Chirotech Technology, Peninsula Laboratories or RSP Amino Acid Analogues, among others.

Within the peptides of the invention derived from the amino acid sequence of SNAP-25 defined by SEQ ID No.1 and chemically modified in an irreversible manner, the preferred sequences are those having an amino acid sequence contained in the sequence of the amino-terminal region of the SNAP-25 protein, defined by SEQ ID No. 2, or of the carboxy-terminal region of the SNAP-25 protein, defined by SEQ ID No. 3, more preferably contained in the region comprised between residues 10 to 22, defined by SEQ ID No.4, or contained in the region comprised between residues 25 to 40, defined by SEQ ID No.5, or contained in the region comprised between residues 65 to 81, defined by SEQ ID No.6, or contained in the region comprised between residues 181 to 206, defined by SEQ ID No.7, more specifically contained in the region comprised between residues 12 to 19, defined by SEQ ID No.8, or contained in the region comprised between residues 26 to 38, defined by SEQ ID No.9, or contained in the region comprised between residues 68 to 79, defined by SEQ ID No.10, and specifically contained in the region comprised between residues 12 to 17, defined by SEQ ID No.11.

The invention also includes peptides that are substantially homologous to the irreversibly chemically modified peptides derived from the amino acid sequence of SNAP-25 protein. "Substantially homologous peptides" are understood as those amino acid sequences which are at least 60%, preferably 80% and more preferably 95% identical to sequence SEQ ID No.1. The "percentage of identity" relates to the percentage of amino acids which are identical between two amino acid sequences which are compared after an optimal alignment of these sequences, where said percentage is merely statistical and the differences between the two amino acid sequences are randomly distributed throughout the sequence. "Optimal alignment" is understood as that alignment of amino acid sequences giving rise to a greater percentage of identity. The percentage of identity is calculated by determining the number of identical positions in which an amino acid is identical in the two compared sequences, dividing the number of identical positions by the number of compared positions and multiplying the result obtained by 100 to obtain the percentage of identity between the two sequences. The sequence comparisons between two amino acid sequences can be carried out manually or by means of computer programs such as the BLAST (Basic Local Alignment Search Tool) algorithm, for example, which can be accessed through the Internet on the website http://www.ncbi.nlm.nih.gov/BLAST/.

Cosmetically or pharmaceutically acceptable salts of the peptides provided by this invention are included within the scope of the present invention. The term "cosmetically or pharmaceutically acceptable salts" includes the salts usually used to form metal salts or acid addition salts, either organic acid addition salts (such as for example, acetate, citrate, oleate, trifluoroacetate, oxalate or gluconate, among others) or inorganic acid addition salts (such as for example chloride, sulfate, borate or carbonate among others). The nature of the salt is not critical, provided that it is cosmetically or pharmaceutically acceptable. The cosmetically or pharmaceutically acceptable salts of the peptides of the invention can be obtained by conventional methods that are well known in the state of the art.

The synthesis of the peptides of the invention can be carried out according to conventional methods known in the state of the art, such as for example, the adaptation of solid phase peptide synthesis methods [Stewart J. M. and Young J. D. (1984) "Solid Phase Peptide Synthesis, 2nd edition", Pierce Chemical Company, Rockford, Ill. Bodanzsky M. and Bodanzsky A. (1984) "The practice of Peptide Synthesis", Springer Verlag, New York; Lloyd-Williams, P., Albericio, F. and Giralt, E. (1997) "Chemical Approaches to the Synthesis of Peptides and Proteins" CRC, Boca Raton (Fla., USA)], solution synthesis, a combination of solid phase synthesis and solution synthesis methods or enzymic synthesis methods [Kullmann W. (1980) "Proteases as catalysts for enzymic syntheses of opioid peptides" J. Biol. Chem. 255, 8234-8238]. The peptides can also be obtained by the fermentation of a bacterial strain that is modified or unmodified by genetic engineering with the aim of producing the desired sequences, or by controlled hydrolysis of proteins of animal or plant origin, preferably plant origin, which releases peptide fragments containing at least the desired sequence.

For example, a method for obtaining the peptides of the invention is that in which a fragment of the peptide of the invention having a free carboxyl group or a reactive derivative thereof is reacted with a complementary fragment having an amino group with at least one free hydrogen atom, with the subsequent formation of an amide type bond, and wherein the functional groups of said fragments that do not participate in the formation of the amide type bond, if they exist, are conveniently protected with temporary or permanent protective groups.

Another example of a method for obtaining the peptides of the invention is that in which a fragment of the peptide of the invention having a leaving group, such as for example the tosyl group, the mesyl group and halogen groups, among others, is reacted with a complementary fragment having an amino group with at least one free hydrogen atom by means of a nucleophilic substitution reaction, and wherein the functional groups of said fragments that do not participate in the formation of the N—C bond, if they exist, are conveniently protected with temporary or permanent protective groups. Examples of protective groups, their insertion and elimination are described in the literature [Greene T. W. (1981) "*Protective groups in organic synthesis*" John Wiley & Sons, New Cork; Atherton B. and Sheppard R. C. (1989) "*Solid Phase Peptide Synthesis: A practical approach*" IRL Oxford University Press]. The term "protective groups" also includes the polymeric supports used in solid phase synthesis.

When the synthesis is carried out completely or partially in solid phase, the following can be mentioned as solid supports to be used in the method of the invention: supports made of polystyrene, polyethylene glycol-grafted polystyrene and the like, such as for example p-methylbenzhydrylamine resins (MBHA [Matsueda G. R. and Stewart J. M. (1981) "*A p-methylbenzhydrylamine resin for improved solid-phase synthesis of peptide amides*" Peptides 2, 45-50], resinas 2-clorotrityl [(a) Barlos K., Gatos D., Kallitsis J., Papaphotiu G., Sotiriu P., Wenqing Y. and Schäfer W. (1989) "*Darstellung geschützter peptid-fragmente unter einsatz substituierter triphenylmethyl-harze*" Tetrahedron Lett. 30, 3943-3946; (b) Barlos K., Gatos D., Kapolos S., Papaphotiu G., Schäfer W. and Wenqing Y. (1989) "*Veresterung von partiell geschützten peptid-fragmenten mit harzen. Einsatz von 2-chlorotritylchlorid zur synthese von Leu15-gastrin I*" Tetrahedron Lett. 30, 3947-3951], TentaGel® resins (Rapp Polymere GmbH), ChemMatrix® resins (Matrix Innovation, Inc) and the like, which may or may not include a labile spacer such as 5-(4-aminometihy-3,5-dimethoxyphenoxy) valeric acid (PAL) [Albericio F., Kneib-Cordonier N., Biancalane S., Gera L., Masada R. I., Hudson D. and Barany G. (1990) "*Preparation and application of the 5-(4-(9-fluorenylmethyloxycarbonyl)aminomethyl-3,5-dimethoxy-phenoxy)-valeric acid (PAL) handle for the solid-phase synthesis of C-terminal peptide amides under mild conditions*" J. Org. Chem. 55, 3730-3743], 2-[4-aminomethyl-(2,4-dimethoxyphenyl) phenoxyacetic acid (AM) [Rink H. (1987) "*Solid-phase synthesis of protected peptide fragments using a trialkoxy-diphenyl-methylester resin*" Tetrahedron Lett. 28, 3787-3790], Wang [Wang S. S. (1973) "*p-Alkoxybenzyl Alcohol Resin and p-Alkoxybenzyloxycarbonylhydrazide Resin for Solid Phase Synthesis of Protected Peptide Frag-* ments" *J. Am. Chem. Soc.* 95, 1328-1333] and the like, allowing the deprotection and simultaneous cleavage of the compound from the polymeric support.

The peptides of the invention can be administered to regulate neuronal exocytosis by any means causing the contact of the compounds with the action site thereof in the body of a mammal, preferably of a human being, in the form of a composition containing them. In this sense, the invention provides a cosmetic or pharmaceutical composition comprising at least one peptide of general formula (I) or its cosmetically or pharmaceutically acceptable salts. Said compositions can be prepared by means of conventional methods known by persons skilled in the art.

The peptides of the invention are used in the cosmetic or pharmaceutical composition of the present invention at cosmetically or pharmaceuticaly effective concentrations to achieve the desired effect; preferably between 0.00000001% (by weight) and 20% (by weight); preferably between 0.00001% (by weight) and 10% (by weight) and more specifically between 0.0001% (by weight) and 5% (by weight).

The peptides object of the present invention have a variable water-solubility, according to the nature of their sequence or the modification in the amino and carboxy-terminal ends that they have. Those which are not water-soluble can be solubilized in conventional cosmetically or pharmaceutically acceptable solvents such as for example ethanol, propanol or isopropanol, propylene glycol, glycerin, butylene glycol or polyethylene glycol.

The pharmaceutically effective amount of the peptides and/or pharmaceutical compositions according to the invention, which must be administered to treat a pathological conditions, as well as its dosage, will depend on a number of factors, including the age, condition of the patient, the severity of the impairment or disease, the method and frequency of administration and on the particular peptides to be used.

The pharmaceutical compositions containing the peptides of the invention can have any form of administration, solid or liquid, for example, and can be administered by any suitable route, for example, orally, nasally, parenterally, rectally, topically or transdermally, for which they will include the necessary pharmaceutical excipients for the formulation of the desired form of administration. In the context of the present invention, the term "parenteral" includes subcutaneous, intradermal, intravascular injections such as for example, intravenous, intramuscular, spinal, intracranial, intra-articular, intrathecal and intraperitoneal injections, as well as any other similar injection or infusion technique. A review of the different pharmaceutical forms of administration of medicinal products and of the necessary excipients for obtaining them can be found in "Tratado de Farmacia Galénica", C. Faulí i Trillo, 1993, Luzán 5, S. A. Ediciones, Madrid, for example.

The peptides of the invention can also be previously incorporated in cosmetic or pharmaceutical sustained release systems and/or carrier systems such as liposomes, milliparticles, microparticles and nanoparticles, sponges, vesicles, micellae, millispheres, microspheres and nanospheres, liposheres, millicapsules, microcapsules and nanocapsules, as well as in microemulsions and nanoemulsions, for the purpose of achieving a greater penetration of the active ingredient and/or improving the pharmacokinetic and pharmacodynamic properties thereof. The controlled release formulations can be prepared by means of methods known in the state of the art and can be administered, for example, by topical administration, including adhesive patches, or orally, rectally or by subcutaneous implantation, or by direct implantation in a specific part of the body, and must preferably release a relatively constant amount of the peptides of the invention. The amount of peptide contained in the controlled release formulation will depend, for example, on the administration site, the kinetics and duration of the release of the peptide of the invention as well as the nature of the condition to be treated or prevented.

The peptides of the present invention can also be adsorbed on solid organic polymers or mineral supports such as talc, bentonite, silica, starch or maltodextrin, among others.

The cosmetic or pharmaceutical preparations containing the peptides of the present invention can be used in different types of formulations for topical application such as for example, and in a non-limiting sense, creams, emulsions of oil and/or silicone in water, emulsions of water in oil and/or silicone, oils, milks, balms, foams, lotions, gels, liniments, serums, soaps, unguents, mousses, ointments, bars, pencils and sprays, including "leave on" and "rinse-off" formulations, and can also be incorporated by means of techniques known by persons skilled in the art to different types of solid accessories such as towelettes, hydrogels, adhesive (or non-adhesive) patches or face masks, or can be incorporated to different make-up line products such as make-up foundations, lotions, make-up removal milks, concealers, eye shadows and lipsticks among others.

The peptides can also be incorporated to fabrics for making garments which are in direct contact with the skin of the body, such that the peptides of the invention are released by the biodegradation of the system for the anchoring to the tissue or by the friction of the garment with the body, by body moisture, by the pH of the skin or by body temperature. Examples of garments, fabrics and means for immobilizing the peptides in the tissues, including microencapsulation, are described in the literature and are known in the state of the art [Schaab C. K. (1986) "*Impregnating Fabrics With Microcapsules*", HAPPI May 1986; Nelson G. (2002) "*Application of microencapsulation in textiles*" *Int. J. Pharm.* 242, 55-62]. Preferred garments are bandages.

The cosmetic or pharmaceutical composition object of the present invention can be applied in the areas of the body requiring treatment or care by means of subcutaneous injection, intradermal injection, steam wrap or by means of iontophoresis for the purpose of achieving a greater penetration of the active ingredient. The area of application is determined by the nature of the condition to be treated. A preferred area for the application is the forehead area having expression wrinkles as well as the space between the eyebrows, the wrinkles and the fine lines around the mouth and/or around the eyes.

The cosmetic or pharmaceutical composition claimed in the present invention can contain additional ingredients commonly used in compositions for caring, cleaning and treating the skin, such as for example and in a non-limiting sense, emulsion agents, emollients, organic solvents, skin conditioners such as for example, humectants, alpha hydroxy acids, moisturizers, vitamins, pigments or dyes, gelling polymers, thickeners, softeners, anti-wrinkle agents, agents that can reduce or treat under-eye bags, whitening or depigmentation agents, exfoliating agents, anti-aging agents, agents capturing free radicals and/or anti-atmospheric pollution agents, NO-synthase inhibiting agents, anti-oxidizing agents, anti-glycation agents, antimicrobial agents, antifungal agents, agents stimulating the synthesis of dermal or epidermal macromolecules and/or able to inhibit their degradation, such as for example agents stimulating collagen synthesis, agents stimulating elastin synthesis, agents stimulating decorin synthesis, agents stimulating laminin synthesis, agents inhibiting collagen degradation, agents inhibiting elastin degradation, agents stimulating fibroblast proliferation, agents stimulating keratinocyte proliferation, agents stimulating keratinocyte differentiation, agents stimulating the synthesis of lipids and components of the stratum corneum (ceramides, fatty acids etc.), skin relaxing agents, agents stimulating glycosaminoglycan synthesis, firming agents, anti-stretch mark agents, calming agents, anti-inflammatory agents, agents acting on capillary circulation and/or microcirculation, agents acting on cell metabolism, agents stimulating and/or inhibiting the synthesis of melanin, agents intended to improve the dermal-epidermal junction, preservatives, perfumes, chelating agents, plant extracts, essential oils, marine extracts, agents coming from biofermentation, mineral salts, cell extracts and sunscreens (organic or mineral photoprotection agents that are active against ultraviolet A and B rays), among others, provided that they are physically and chemically compatible with the rest of the components of the composition and especially with the peptides of general formula (I) contained in the composition of the present invention. The nature of said additional ingredients can be synthetic or natural, such as for example plant extracts, or can come form a biofermentation process.

An additional aspect of the present invention relates to a cosmetic or pharmaceutical composition containing a cosmetically or pharmaceutically effective amount of at least one peptide of the invention and also a cosmetically or pharmaceutically effective amount of at least one extract with anti-wrinkle and/or anti-aging activity such as for example and in a non-limiting sense, Vitis vinifera, Rosa canina, Curcuma longa, Iris pellicle, Theobroma cacao, Ginkgo biloba, or Dunaliella salina extracts, among others or of also at least one synthetic compound, extract or biofermentation product with anti-wrinkle and/or anti-aging activity as for example and in a non-limiting sense Matrixyl® marketed by Sederma, Vialox® or Syn-ake® marketed by Pentapharm, Myoxinol™ marketed by Cognis, Algisum C® or Hydroxyprolisilane CN®, marketed by Exsymol, Argireline®, Leuphasyl®, Aldenine®, Decorinyl®, Decorinol® or Lipochroman® marketed by Lipotec, Kollaren® marketed by Institut Europeen de Biologie Cellulaire, Collaxyl® or Quintescine® marketed by Vincience, $Ca^{2+}$ channel antagonists such as alverine, manganese or magnesium salts, certain secondary or tertiary amines, retinol and its derivatives, idebenone and its derivatives, Coenzyme Q10 and its derivatives, boswellic acid and its derivatives, gamma-aminobutyric acid or chloride channel agonists among others.

The compositions of the present invention can contain or can be co-administered with analgesic compounds and/or anti-inflammatory compounds for the purpose of reducing the swelling and the irritation associated to sensitive skin. Steroidal type compounds such as hydrocortisone, non-steroidal type compounds such as paracetamol or acetylsalicylic acid or natural extracts or essential oils with intrinsic analgesic and anti-inflammatory activity.

The peptides of the invention have a mechanism of action similar to that of botulinum toxin, inhibiting neuronal exocytosis, therefore it can be considered that the peptides will show efficacy in the treatment of facial wrinkles and/or facial asymmetry as well as the treatment of the conditions presenting muscle spasticity, such as dystonias, strabismus, blepharospasm, torticollis, tics, etc.

An additional aspect of this invention therefore relates to the use of at least one peptide of general formula (I) in the preparation of a cosmetic or pharmaceutical composition for the treatment of those conditions of mammals, preferably humans, which require regulating neuronal exocytosis. Another aspect of the present invention relates to the use of at least one peptide of general formula (I) in the preparation of a cosmetic or pharmaceutical composition for treating, cleaning or caring for the skin. An additional aspect of this invention relates to the use of at least one irreversibly chemically modified peptide derived from the amino acid sequence of the SNAP-25 protein in the preparation of a cosmetic or pharmaceutical composition for reducing and/or eliminating facial asymmetry and facial wrinkles, preferably expression wrinkles. Another additional aspect of this invention relates to the use of at least one irreversibly chemically modified peptide derived from the amino acid sequence of the SNAP-25 protein in the preparation of a cosmetic or pharmaceutical composition for treating those neurological disorders or pathologies presenting muscle spasticity, such as dystonias, strabismus, blepharospasm, torticollis, tics, etc.

Another aspect of the present invention relates to a cosmetic or pharmaceutical method for treating those conditions of mammals which require regulating neuronal exocytosis, preferably of humans, comprising the administration of an effective amount of at least one peptide of general formula (I), preferably in the form of a cosmetic or pharmaceutical composition comprising it. The present invention further provides a cosmetic or pharmaceutical method for reducing and/or eliminating facial wrinkles or for treating facial asymmetry, comprising the application in the skin of the face of a cosmetic or pharmaceutical composition containing at least one peptide of the invention or its cosmetically or pharmaceutically acceptable salts. The present invention also provides a cosmetic or pharmaceutical method for treating those neurological disorders or pathologies presenting muscle spasticity, such as dystonias, strabismus, blepharospasm, torticollis, tics, etc., comprising the application of a cosmetic or pharmaceutical composition containing at least one peptide of the invention or its cosmetically or pharmaceutically acceptable salts.

The frequency of application can vary extensively, depending on the needs of each subject, a range of application from once a month up to 10 times a day, preferably from once a week up to 4 times a day, more preferably from three times a week up to twice a day, even more preferably one a day, being suggested.

The preferred cosmetic or pharmaceutical method is that in which the application is carried out in those areas of the face or forehead marked with expression wrinkles, preferably on the wrinkles around the mouth and/or the eyes, and/or in the wrinkles of the forehead and/or on the wrinkles of the space between the eyebrows.

DESCRIPTION OF THE DRAWINGS

FIG. 1 shows that in the presence of the peptides of the invention at a concentration of 0.1 mM, the release of [$^3$H]-L-glutamate from primary cultures of rat hippocampus neurons was inhibited by more than 40%, indicating that the compounds are neuronal exocytosis inhibitors. The inhibition of the release [$^3$H]-L-glutamate by the unmodified peptide derived from the amino acid sequence of the SNAP-25 protein defined by SEQ ID No.11 at the same concentration was only 5%, concentrations in the range of 30 times greater (3 mM) being required to reach inhibition levels which can be compared to those of the irreversible modified peptides.

EMBODIMENTS

The following specific examples provided herein are useful for illustrating the nature of the present invention. These examples are included solely for illustrative purposes and must not be interpreted as limitations to the invention claimed herein.

General Methodology

Chemical Synthesis

All the synthetic processes are carried out in polypropylene syringes equipped with porous polyethylene disks. All the reagents and solvents are of a quality for synthesis and are used without any additional treatment. The solvents and reagents are eliminated by suction. The elimination of the Fmoc group is carried out with piperidine—DMF (2:8, v/v) (1×1 min, 1×5 min; 5 mL/g resin) [Lloyd-Williams P., Albericio F. and Giralt, E. (1997) *"Chemical Approaches to the Synthesis of Peptides and Proteins"* CRC, Boca Raton (Fla., USA)]. The washings between the steps of deprotection, coupling and once again deprotection have been carried out with DMF (3×1 min) using 10 mL of solvent/g of resin. The coupling reactions have been carried out with 3 mL of solvent/g of resin. The control of the couplings is carried out by means of the ninhydrin test [Kaiser E., Colescott R. L., Bossinger C. D. and Cook P. I. (1970) *"Color test for detection of free terminal amino groups in the solid-phase synthesis of peptides"* Anal. Biochem. 34, 595-598]. All the synthetic transformations and washings have been carried out at 25° C.

The electrospray mass spectroscopy analysis was carried out in LCMS-QP 8000 Shimadzu equipment (Kyoto, Japan), using a mixture of MeCN:$H_2O$ 4:1 (+0.1% TFA) as a mobile phase and a flow rate of 0.2 mL/min.

Abbreviations

The abbreviations used for the amino acids follow the rules of the IUPAC-IUB Commission on Biochemical Nomenclature specified in *Eur. J. Biochem.* (1984) 138, 9-37 and in *J. Biol. Chem.* (1989) 264, 633-673.

AM, 2-[4-aminomethyl-(2,4-dimethoxyphenyl)]-phenoxyacetic acid; BoNT A, botulinum toxin serotype A; cps, centipoise; DCM, dichloromethane; DIEA, N,N-diisopropylethylamine; DIPCDI, N,N'-diisopropylcarbodiimide; DMF, N,N-dimethylformamide; DPPC, dipalmitoylphosphatidylcholine; eq., equivalent; Fmoc, fluorenylmethoxycarbonyl; HOBt, 1-hydroxybenzotriazole; INCI, International Nomenclature of Cosmetic Ingredients; MBHA, p-methylbenzhydrylamina; MeCN, acetonitrile; MLV, multilaminar vesicles; MeOH, methanol; NMP, N-methylpyrrolidone; Pbf, 2,2,4,6,7-pentamethyldihydrobenzofuran-5-sulfonyl; PEG, polyethylene glycol; $PEG_n$, —[NH—$CH_2$—($CH_2CH_2O$)$_3$—($CH_2$)$_3$—NH—CO—$CH_2CH_2$—CO-]$_n$; rpm, revolutions per minute; SNAP-25, synaptosomal associated protein (25 kDa); tBu, tert-butyl; TFA, trifluoroacetic acid; THF, tetrahydrofuran; ULV, unilaminar vesicles.

Example 1

Obtaining Fmoc-Glu(OtBu)-Glu(OtBu)-Met-Gln-Arg(Pbf)-Arg(Pbf)-AM-MBHA 151.3 g of the Fmoc-AM-MBHA resin with a functionalization of 0.628 mmol/g (95 mmol, 1 eq.) are treated with piperidine—DMF according to the described general protocol for the purpose of eliminating the Fmoc group. 154.1 g of Fmoc-L-Arg(Pbf)-OH (237 mmol, 2.5 eq.) are incorporated to the unprotected resin in the presence of DIPCDI (36.6 mL, 237 mmol, 2.5 eq.) and HOBt (35.6 g, 237 mmol, 2.5 eq.) using DMF as a solvent for 1 h.

The resin is subsequently washed as described in the general methods and the treatment for deprotecting the Fmoc group is repeated to incorporate the next amino acid. By following the described protocols, 154.1 g of Fmoc-L-Arg(Pbf)-OH (237 mmol, 2.5 eq.), 87.5 g of Fmoc-Gln-OH (474 mmol, 5 eq.), 88.2 g of Fmoc-L-Met-OH (237 mmol, 2.5 eq.), 105.3 g of Fmoc-L-Glu(OtBu)-OH (237 mmol, 2.5 eq.) and 105.3 g of Fmoc-L-Glu(OtBu)-OH (237 mmol, 2.5 eq.) are sequentially coupled with the presence in each coupling of 36.5 g of HOBt (237 mmol, 2.5 eq.) and 36.6 mL of DIPCDI (237 mmol, 2.5 eq.), except in the step of incorporating Fmoc-L-Gln-OH in which 71.3 g of HOBt (474 mmol, 5 eq.) are used.

The Fmoc-Glu(OtBu)-Glu(OtBu)-Met-Gln-Arg(Pbf)-Arg(Pbf)-AM-MBHA obtained is washed with DMF (5×1 min), DCM (4×1 min), diethyl ether (4×1 min) and is dried under vacuum.

Example 2

Obtaining ($CH_3$—($CH_2$)$_m$—CO-SEQ ID No.11-$NH_2$)

The amino-terminal Fmoc group of 1.68 g of Fmoc-Glu(OtBu)-Glu(OtBu)-Met-Gln-Arg(Pbf)-Arg(Pbf)-AM-MBHA (0.5 mmol, 0.296 mmol/g, 1 eq.) is deprotected as described in general methods, and $CH_3$—($CH_2$)$_m$—COOH (5 mmol, 10 eq.) predissolved in DMF (10 mL) is incorporated in the presence of 770 mg of HOBt (5 mmol, 10 eq.) and 770 μL of DIPCDI (5 mmol, 10 eq.). It is allowed to react for 15 h, after which the resin is washed with THF (5×1 min), DCM (5×1 min), DMF (5×1 min), MeOH (5×1 min), DMF (5×1 min), THF (5×1 min), DMF (5×1 min), DCM (4×1 min), ether (3×1 min), and is dried under vacuum.

1.00 g of the dry peptidyl-resin are treated with 15 mL of TFA-$^iPr_3Si$—$H_2O$ (90:5:5) for 2 h at room temperature. The filtrates are collected on cold diethyl ether (100 mL), centrifuged for 5 min at 4000 rpm and the ether solution is decanted. The washings are repeated with ether 5 times. The final precipitate is dried under vacuum.

| m | amount obtained | purity | theoretical MW | experimental MW |
|---|---|---|---|---|
| 6 | 291.2 mg | 88.2% | $[M + H]^+ = 972.5$ | $[M + H^+] = 973.8$ <br> $[M + 2H^+/2] = 487.5$ |
| 8 | 240.1 mg | 87.2% | $[M + H]^+ = 1000.5$ | $[M + H^+] = 1001.8$ <br> $[M + 2H^+/2] = 501.5$ |
| 12 | 327.5 mg | 80.7% | $[M + H]^+ = 1056.6$ | $[M + H^+] = 1057.8$ <br> $[M + 2H^+/2] = 529.5$ |
| 14 | 292.8 mg | 80.9% | $[M + H]^+ = 1084.6$ | $[M + H^+] = 1085.9$ <br> $[M + 2H^+/2] = 543.7$ |
| 20 | 233.7 mg | 85.1% | $[M + H]^+ = 1168.74$ | $[M + H^+] = 1170.0$ <br> $[M + 2H^+/2] = 585.7$ |

Example 3

Obtaining (Ac-$PEG_n$-SEQ ID No.11-$NH_2$)

The amino-terminal Fmoc group of 321.0 mg of Fmoc-Glu(OtBu)-Glu(OtBu)-Met-Gln-Arg(Pbf)-Arg(Pbf)-AM- MBHA (0.095 mmol, 0.296 mmol/g, 1 eq.) is deprotected as described in general methods, and Fmoc-PEG$_1$-OH (2.5 eq.) predissolved in NMP, is added in the presence of 36.5 mg of HOBt (0.237 mmol, 2.5 eq.) and 36.6 μL of DIPCDI (0.237 mmol, 2.5 eq.), for 40-60 min. The amino-terminal Fmoc group as describe in general methods and the reaction for incorporating Fmoc-PEG$_1$-OH and the dsprotection of Fmoc is carried out (n–1) times, where n=1-100 to obtain the different derivatives. The acetylation of amino-terminal end is carried out with con Ac$_2$O (2.5 eq.) and DIEA (2.5 eq.) in DMF for 30 min.

The Ac-PEG$_n$-Glu(OtBu)-Glu(OtBu)-Met-Gln-Arg(Pbf)-Arg(Pbf)-AM-MBHA resin is washed with DMF (5×1 min), DCM (4×1 min), diethyl ether (4×1 min) and is dried under vacuum.

22.4 mg of Ac-PEG$_n$-Glu(OtBu)-Glu(OtBu)-Met-Gln-Arg(Pbf)-Arg(Pbf)-AM-MBHA are treated with 1.57 mL of the TFA-$^i$Pr$_3$Si—H$_2$O (95:2.5:2.5) cocktail for 5 min at 0° C. followed by 90 min at room temperature. The filtrates are collected on cold diethyl ether (10 mL), centrifgured for 5 min at 4000 rpm and and the ether solution is decanted. The washings are repeated with ether 5 times. The final oily residue is redissolved in MeCN:H$_2$O 1:1 and lyophilized.

| n | amount obtained | purity | theoretical MW | experimental MW |
|---|---|---|---|---|
| 1 | 7.7 mg | 72% | [M + H]$^+$ = 1191.6 | [M + 2H$^+$/2] = 596.4 |
|   |        |     |                      | [M + 3H$^+$/3] = 398.0 |
| 2 | 10.0 mg | 60% | [M + H]$^+$ = 1494.7 | [M + 2H$^+$/2] = 747.6 |
|   |        |     |                      | [M + 3H$^+$/3] = 498.7 |
| 3 | 10.4 mg | 64% | [M + H]$^+$ = 1796.1 | [M + 2H$^+$/2] = 898.7 |
|   |        |     |                      | [M + 3H$^+$/3] = 599.6 |
|   |        |     |                      | [M + 4H$^+$/4] = 449.8 |
| 4 | 13.7 mg | 65% | [M + H]$^+$ = 2099.5 | [[M + 2H$^+$/2] = 1050 |
|   |        |     |                      | [M + 3H$^+$/3] = 700.4 |
|   |        |     |                      | [M + 4H$^+$/4] = 525.4 |
|   |        |     |                      | [M + 5H$^+$/5] = 420.5 |
| 5 | 10.4 mg | 65% | [M + H]$^+$ = 2400.3 | [M + 2H$^+$/2] = 1201.1 |
|   |        |     |                      | [M + 3H$^+$/3] = 801.1 |
|   |        |     |                      | [M + 4H$^+$/4] = 601.0 |
|   |        |     |                      | [M + 5H$^+$/5] = 481.0 |
|   |        |     |                      | [M + 6H$^+$/6] = 400.9 |

Example 4

Obtaining (Ac-SEQ ID No.11-NH—(CH$_2$)$_s$—CH$_3$)

2.10 g of Fmoc-L-Arg(Pbf)-OH (3.23 mmol, 1 equiv) dissolved in 20 mL of DCM to which 500 μL of DIEA (2.9 mmol, 0.90 equiv) have been added are incorporated to the dry 2-chlorotrityl resin (2.0 g, 3.3 mmol). It is left stirring for 5 minutes, after which 1 mL of DIEA (5.9 mmol, 1.81 equiv) is added. It is allowed to react for 40 minutes. The remaining chloride groups are protected by treatment with 1.6 mL of MeOH.

The amino-terminal Fmoc group is deprotected as described in general methods and 3.24 g of Fmoc-L-Arg(Pbf)-OH (5 mmol, 5 equiv) are incorporated to 1 mmol of the aminoacyl-resin Fmoc-L-Arg(Pbf)-ClTrt® in the presence of DIPCDI (770 μL, 5 mmol, 5 equiv) and HOBt (770 g, 5 mmol, 5 equiv) using DMF as a solvent for 1 hour. The resin is subsequently washed as described in general methods and the treatment for deprotecting the Fmoc group is repeated to incorporate the next amino acid. By following the described protocols, 1.84 g of Fmoc-L-Gln-OH (5 mmol, 5 equiv), 1.86 g of Fmoc-L-Met-OH (5 mmol, 5 equiv), 2.12 g of Fmoc-L-Glu(OtBu)-OH and 2.12 g of Fmoc-L-Glu(OtBu)-OH (5 mmol, 5 equiv) are coupled sequentially in the presence in each coupling of 770 mg of HOBt (5 mmol, 5 equiv) and 770 μL of DIPCDI (5 mmol, 5 equiv), except in the step in which Fmoc-L-Gln-OH is incorporated, in which step 1.54 g of HOBt (10 mmol, 10 equiv) are added.

The amino-terminal Fmoc group is deprotected as described in general methods, the peptidyl-resin is treated for 30 min with 2.36 mL of acetic anhydride (25 mmol, 25 equiv) in the presence of 4.28 mL of DIEA (25 mmol, 25 equiv) using DMF as a solvent, it is washed with DMF (5×1 min), DCM (4×1 min), diethyl ether (4×1 min) and is dried under vacuum.

The completely protected peptide [Ac-Glu(OtBu)-Glu(OtBu)-Met-Gln-Arg(Pbf)-Arg(Pbf)-OH] is obtained by treating for 5 min the peptidyl-resin, previously dried under vacuum in the presence of KOH, with a 3% solution of TFA in DCM. The filtrates are collected on cold diethyl ether and the treatment is repeated three times. The ether solutions are rotary evaporated to dryness and at room temperature; the precipitate is resuspended in 50% MeCN in H$_2$O and is lyophilized. 279 mg of the raw product obtained (367 μmol) are weighed in a balloon, 3 equiv of CH$_3$—(CH$_2$)$_s$—NH$_2$ and 30 mL of anhydrous DMF are added. 120 μL of DIPCDI (2 equiv) are added, and it is allowed to react under magnetic stirring at 47° C. The reaction is controlled by means of HPLC by the disappearance of the initial product, being complete after 24 h. The solvent is evaporated to dryness and co-evaporated twice with DCM. The obtained residue [Ac-Glu(OtBu)-Glu(OtBu)-Met-Gln-Arg(Pbf)-Arg(Pbf)-NH—(CH$_2$)$_s$—CH$_3$] is resuspended in 50 mL of a mixture of TFA-$^i$Pr$_3$Si—H$_2$O (90:5:5) and is allowed to react for 30 min at room temperature. 250 mL of cold diethyl ether are added, the solvent is rotary evaporated and two additional co-evaporations are carried out with ether. The residue is dissolved in a mixture of 50% MeCN in H$_2$O and is lyophilized.

| s | obtained amount | purity | theoretical MW | experimental MW |
|---|---|---|---|---|
| 11 | 391.2 mg | 92.2% | [M + H]$^+$ = 1058.3 | [M + H$^+$] = 1057.9 |
|    |          |       |                      | [M + 2H$^+$/2] = 529.8 |
| 15 | 424.5 mg | 90.5% | [M + H]$^+$ = 1114.74 | [M + H$^+$] = 1114.0 |
|    |          |       |                       | [M + 2H$^+$/2] = 557.6 |

Example 5

According to the general protocols described in Examples 1 to 4, by routinely varying the nature of the reagents and the peptide sequences, the following irreversibly chemically modified peptides derived from the sequence of the SNAP-25 protein, included in the scope of the present invention, were additionally obtained.

| | Structure | Molecular weight |
|---|---|---|
| 1. | CH₃—(CH₂)₄—CO-EEMQRR-NH₂ | 945.1 |
| 2. | CH₃—(CH₂)₁₀—CO-EEMQRR-NH₂ | 1029.2 |
| 3. | CH₃—(CH₂)₁₆—CO-EEMQRR-NH₂ | 1113.4 |
| 4. | CH₃—(CH₂)₁₈—CO-EEMQRR-NH₂ | 1041.4 |
| 5. | CH₃—(CH₂)₄—CO-EEMQRRA-NH₂ | 1016.4 |
| 6. | CH₃—(CH₂)₆—CO-EEMQRRA-NH₂ | 1044.4 |
| 7. | CH₃—(CH₂)₈—CO-EEMQRRA-NH₂ | 1072.5 |
| 8. | CH₃—(CH₂)₁₀—CO-EEMQRRA-NH₂ | 1100.5 |
| 9. | CH₃—(CH₂)₁₂—CO-EEMQRRA-NH₂ | 1128.6 |
| 10. | CH₃—(CH₂)₁₄—CO-EEMQRRA-NH₂ | 1156.6 |
| 11. | CH₃—(CH₂)₁₆—CO-EEMQRRA-NH₂ | 1184.7 |
| 12. | CH₃—(CH₂)₁₈—CO-EEMQRRA-NH₂ | 1112.7 |
| 13. | CH₃—(CH₂)₂₀—CO-EEMQRRA-NH₂ | 1240.8 |
| 14. | CH₃—(CH₂)₄—CO-EEMQRRAD-NH₂ | 1131.3 |
| 15. | CH₃—(CH₂)₆—CO-EEMQRRAD-NH₂ | 1159.3 |
| 16. | CH₃—(CH₂)₈—CO-EEMQRRAD-NH₂ | 1187.4 |
| 17. | CH₃—(CH₂)₁₀—CO-EEMQRRAD-NH₂ | 1215.4 |
| 18. | CH₃—(CH₂)₁₂—CO-EEMQRRAD-NH₂ | 1243.5 |
| 19. | CH₃—(CH₂)₁₄—CO-EEMQRRAD-NH₂ | 1271.5 |
| 20. | CH₃—(CH₂)₁₆—CO-EEMQRRAD-NH₂ | 1299.6 |
| 21. | CH₃—(CH₂)₁₈—CO-EEMQRRAD-NH₂ | 1227.6 |
| 22. | CH₃—(CH₂)₂₀—CO-EEMQRRAD-NH₂ | 1355.7 |
| 23. | CH₃—(CH₂)₄—CO-ELEEMQRRADQLA-NH₂ | 1685.9 |
| 24. | CH₃—(CH₂)₆—CO-ELEEMQRRADQLA-NH₂ | 1713.9 |
| 25. | CH₃—(CH₂)₈—CO-ELEEMQRRADQLA-NH₂ | 1742.0 |
| 26. | CH₃—(CH₂)₁₀—CO-ELEEMQRRADQLA-NH₂ | 1770.0 |
| 27. | CH₃—(CH₂)₁₂—CO-ELEEMQRRADQLA-NH₂ | 1798.1 |
| 28. | CH₃—(CH₂)₁₄—CO-ELEEMQRRADQLA-NH₂ | 1826.1 |
| 29. | CH₃—(CH₂)₁₆—CO-ELEEMQRRADQLA-NH₂ | 1854.2 |
| 30. | CH₃—(CH₂)₁₈—CO-ELEEMQRRADQLA-NH₂ | 1782.2 |
| 31. | CH₃—(CH₂)₂₀—CO-ELEEMQRRADQLA-NH₂ | 1910.3 |
| 32. | CH₃—(CH₂)₄—CO-ADESLESTRRMLQLVEESKDAGI-NH₂ | 2675.0 |
| 33. | CH₃—(CH₂)₆—CO-ADESLESTRRMLQLVEESKDAGI-NH₂ | 2703.0 |
| 34. | CH₃—(CH₂)₈—CO-ADESLESTRRMLQLVEESKDAGI-NH₂ | 2731.1 |
| 35. | CH₃—(CH₂)₁₀—CO-ADESLESTRRMLQLVEESKDAGI-NH₂ | 2759.1 |
| 36. | CH₃—(CH₂)₁₂—CO-ADESLESTRRMLQLVEESKDAGI-NH₂ | 2787.2 |
| 37. | CH₃—(CH₂)₁₄—CO-ADESLESTRRMLQLVEESKDAGI-NH₂ | 2815.2 |
| 38. | CH₃—(CH₂)₁₆—CO-ADESLESTRRMLQLVEESKDAGI-NH₂ | 2843.3 |
| 39. | CH₃—(CH₂)₁₈—CO-ADESLESTRRMLQLVEESKDAGI-NH₂ | 2771.3 |
| 40. | CH₃—(CH₂)₂₀—CO-ADESLESTRRMLQLVEESKDAGI-NH₂ | 2899.4 |
| 41. | CH₃—(CH₂)₄—CO-DEANQRATKMLGSG-NH₂ | 1574.8 |
| 42. | CH₃—(CH₂)₆—CO-DEANQRATKMLGSG-NH₂ | 1602.8 |
| 43. | CH₃—(CH₂)₈—CO-DEANQRATKMLGSG-NH₂ | 1630.9 |
| 44. | CH₃—(CH₂)₁₀—CO-DEANQRATKMLGSG-NH₂ | 1658.9 |
| 45. | CH₃—(CH₂)₁₂—CO-DEANQRATKMLGSG-NH₂ | 1687.0 |
| 46. | CH₃—(CH₂)₁₄—CO-DEANQRATKMLGSG-NH₂ | 1715.0 |
| 47. | CH₃—(CH₂)₁₆—CO-DEANQRATKMLGSG-NH₂ | 1743.1 |
| 48. | CH₃—(CH₂)₁₈—CO-DEANQRATKMLGSG-NH₂ | 1671.1 |
| 49. | CH₃—(CH₂)₂₀—CO-DEANQRATKMLGSG-NH₂ | 1799.2 |
| 50. | CH₃—(CH₂)₄—CO-EEMQRRADQ-NH₂ | 1259.4 |
| 51. | CH₃—(CH₂)₆—CO-EEMQRRADQ-NH₂ | 1287.4 |
| 52. | CH₃—(CH₂)₈—CO-EEMQRRADQ-NH₂ | 1315.5 |
| 53. | CH₃—(CH₂)₁₀—CO-EEMQRRADQ-NH₂ | 1343.5 |
| 54. | CH₃—(CH₂)₁₂—CO-EEMQRRADQ-NH₂ | 1371.6 |
| 55. | CH₃—(CH₂)₁₄—CO-EEMQRRADQ-NH₂ | 1399.6 |
| 56. | CH₃—(CH₂)₁₆—CO-EEMQRRADQ-NH₂ | 1427.7 |
| 57. | CH₃—(CH₂)₁₈—CO-EEMQRRADQ-NH₂ | 1355.7 |
| 58. | CH₃—(CH₂)₂₀—CO-EEMQRRADQ-NH₂ | 1483.8 |
| 59. | CH₃—(CH₂)₄—CO-EEMQRRADQL-NH₂ | 1372.6 |
| 60. | CH₃—(CH₂)₆—CO-EEMQRRADQL-NH₂ | 1400.6 |
| 61. | CH₃—(CH₂)₈—CO-EEMQRRADQL-NH₂ | 1428.7 |
| 62. | CH₃—(CH₂)₁₀—CO-EEMQRRADQL-NH₂ | 1456.7 |
| 63. | CH₃—(CH₂)₁₂—CO-EEMQRRADQL-NH₂ | 1484.8 |
| 64. | CH₃—(CH₂)₁₄—CO-EEMQRRADQL-NH₂ | 1512.8 |
| 65. | CH₃—(CH₂)₁₆—CO-EEMQRRADQL-NH₂ | 1540.9 |
| 66. | CH₃—(CH₂)₁₈—CO-EEMQRRADQL-NH₂ | 1468.9 |
| 67. | CH₃—(CH₂)₂₀—CO-EEMQRRADQL-NH₂ | 1597.0 |
| 68. | CH₃—(CH₂)₄—CO-ELEEMQRR-NH₂ | 1187.4 |
| 69. | CH₃—(CH₂)₆—CO-ELEEMQRR-NH₂ | 1215.4 |
| 70. | CH₃—(CH₂)₈—CO-ELEEMQRR-NH₂ | 1243.5 |
| 71. | CH₃—(CH₂)₁₀—CO-ELEEMQRR-NH₂ | 1271.5 |
| 72. | CH₃—(CH₂)₁₂—CO-ELEEMQRR-NH₂ | 1299.6 |
| 73. | CH₃—(CH₂)₁₄—CO-ELEEMQRR-NH₂ | 1327.6 |
| 74. | CH₃—(CH₂)₁₆—CO-ELEEMQRR-NH₂ | 1355.7 |
| 75. | CH₃—(CH₂)₁₈—CO-ELEEMQRR-NH₂ | 1283.7 |
| 76. | CH₃—(CH₂)₂₀—CO-ELEEMQRR-NH₂ | 1411.8 |
| 77. | CH₃—(CH₂)₄—CO-ELEEMQRRA-NH₂ | 1258.5 |
| 78. | CH₃—(CH₂)₆—CO-ELEEMQRRA-NH₂ | 1286.5 |

| | Structure | Molecular weight |
|---|---|---|
| 79. | $CH_3-(CH_2)_8-CO$-ELEEMQRRA-$NH_2$ | 1314.6 |
| 80. | $CH_3-(CH_2)_{10}-CO$-ELEEMQRRA-$NH_2$ | 1342.6 |
| 81. | $CH_3-(CH_2)_{12}-CO$-ELEEMQRRA-$NH_2$ | 1370.7 |
| 82. | $CH_3-(CH_2)_{14}-CO$-ELEEMQRRA-$NH_2$ | 1398.7 |
| 83. | $CH_3-(CH_2)_{16}-CO$-ELEEMQRRA-$NH_2$ | 1426.8 |
| 84. | $CH_3-(CH_2)_{18}-CO$-ELEEMQRRA-$NH_2$ | 1354.8 |
| 85. | $CH_3-(CH_2)_{20}-CO$-ELEEMQRRA-$NH_2$ | 1482.9 |
| 86. | $CH_3-(CH_2)_4-CO$-ELEEMQRRAD-$NH_2$ | 1373.6 |
| 87. | $CH_3-(CH_2)_6-CO$-ELEEMQRRAD-$NH_2$ | 1401.6 |
| 88. | $CH_3-(CH_2)_8-CO$-ELEEMQRRAD-$NH_2$ | 1429.7 |
| 89. | $CH_3-(CH_2)_{10}-CO$-ELEEMQRRAD-$NH_2$ | 1457.7 |
| 90. | $CH_3-(CH_2)_{12}-CO$-ELEEMQRRAD-$NH_2$ | 1485.8 |
| 91. | $CH_3-(CH_2)_{14}-CO$-ELEEMQRRAD-$NH_2$ | 1513.8 |
| 92. | $CH_3-(CH_2)_{16}-CO$-ELEEMQRRAD-$NH_2$ | 1541.9 |
| 93. | $CH_3-(CH_2)_{18}-CO$-ELEEMQRRAD-$NH_2$ | 1469.9 |
| 94. | $CH_3-(CH_2)_{20}-CO$-ELEEMQRRAD-$NH_2$ | 1598.0 |
| 95. | $CH_3-(CH_2)_4-CO$-ELEEMQRRADQ-$NH_2$ | 1501.7 |
| 96. | $CH_3-(CH_2)_6-CO$-ELEEMQRRADQ-$NH_2$ | 1529.7 |
| 97. | $CH_3-(CH_2)_8-CO$-ELEEMQRRADQ-$NH_2$ | 1557.8 |
| 98. | $CH_3-(CH_2)_{10}-CO$-ELEEMQRRADQ-$NH_2$ | 1585.8 |
| 99. | $CH_3-(CH_2)_{12}-CO$-ELEEMQRRADQ-$NH_2$ | 1613.9 |
| 100. | $CH_3-(CH_2)_{14}-CO$-ELEEMQRRADQ-$NH_2$ | 1641.9 |
| 101. | $CH_3-(CH_2)_{16}-CO$-ELEEMQRRADQ-$NH_2$ | 1670.0 |
| 102. | $CH_3-(CH_2)_{18}-CO$-ELEEMQRRADQ-$NH_2$ | 1598.0 |
| 103. | $CH_3-(CH_2)_{20}-CO$-ELEEMQRRADQ-$NH_2$ | 1726.1 |
| 104. | $CH_3-(CH_2)_4-CO$-ELEEMQRRADQL-$NH_2$ | 1614.9 |
| 105. | $CH_3-(CH_2)_6-CO$-ELEEMQRRADQL-$NH_2$ | 1642.9 |
| 106. | $CH_3-(CH_2)_8-CO$-ELEEMQRRADQL-$NH_2$ | 1671.0 |
| 107. | $CH_3-(CH_2)_{10}-CO$-ELEEMQRRADQL-$NH_2$ | 1699.0 |
| 108. | $CH_3-(CH_2)_{12}-CO$-ELEEMQRRADQL-$NH_2$ | 1727.1 |
| 109. | $CH_3-(CH_2)_{14}-CO$-ELEEMQRRADQL-$NH_2$ | 1755.1 |
| 110. | $CH_3-(CH_2)_{16}-CO$-ELEEMQRRADQL-$NH_2$ | 1783.2 |
| 111. | $CH_3-(CH_2)_{18}-CO$-ELEEMQRRADQL-$NH_2$ | 1711.2 |
| 112. | $CH_3-(CH_2)_{20}-CO$-ELEEMQRRADQL-$NH_2$ | 1839.3 |
| 113. | $CH_3-(CH_2)_4-CO$-KNLTDL-$NH_2$ | 800.0 |
| 114. | $CH_3-(CH_2)_6-CO$-KNLTDL-$NH_2$ | 828.0 |
| 115. | $CH_3-(CH_2)_8-CO$-KNLTDL-$NH_2$ | 856.1 |
| 116. | $CH_3-(CH_2)_{10}-CO$-KNLTDL-$NH_2$ | 884.1 |
| 117. | $CH_3-(CH_2)_{12}-CO$-KNLTDL-$NH_2$ | 912.2 |
| 118. | $CH_3-(CH_2)_{14}-CO$-KNLTDL-$NH_2$ | 940.2 |
| 119. | $CH_3-(CH_2)_{16}-CO$-KNLTDL-$NH_2$ | 968.3 |
| 120. | $CH_3-(CH_2)_{18}-CO$-KNLTDL-$NH_2$ | 896.3 |
| 121. | $CH_3-(CH_2)_{20}-CO$-KNLTDL-$NH_2$ | 1024.4 |
| 122. | $CH_3-(CH_2)_4-CO$-LEEMQRR-$NH_2$ | 1058.3 |
| 123. | $CH_3-(CH_2)_6-CO$-LEEMQRR-$NH_2$ | 1086.3 |
| 124. | $CH_3-(CH_2)_8-CO$-LEEMQRR-$NH_2$ | 1114.4 |
| 125. | $CH_3-(CH_2)_{10}-CO$-LEEMQRR-$NH_2$ | 1142.4 |
| 126. | $CH_3-(CH_2)_{12}-CO$-LEEMQRR-$NH_2$ | 1170.5 |
| 127. | $CH_3-(CH_2)_{14}-CO$-LEEMQRR-$NH_2$ | 1198.5 |
| 128. | $CH_3-(CH_2)_{16}-CO$-LEEMQRR-$NH_2$ | 1226.6 |
| 129. | $CH_3-(CH_2)_{18}-CO$-LEEMQRR-$NH_2$ | 1154.6 |
| 130. | $CH_3-(CH_2)_{20}-CO$-LEEMQRR-$NH_2$ | 1282.7 |
| 131. | $CH_3-(CH_2)_4-CO$-LEEMQRRA-$NH_2$ | 1129.4 |
| 132. | $CH_3-(CH_2)_6-CO$-LEEMQRRA-$NH_2$ | 1157.4 |
| 133. | $CH_3-(CH_2)_8-CO$-LEEMQRRA-$NH_2$ | 1185.5 |
| 134. | $CH_3-(CH_2)_{10}-CO$-LEEMQRRA-$NH_2$ | 1213.5 |
| 135. | $CH_3-(CH_2)_{12}-CO$-LEEMQRRA-$NH_2$ | 1241.6 |
| 136. | $CH_3-(CH_2)_{14}-CO$-LEEMQRRA-$NH_2$ | 1269.6 |
| 137. | $CH_3-(CH_2)_{16}-CO$-LEEMQRRA-$NH_2$ | 1297.7 |
| 138. | $CH_3-(CH_2)_{18}-CO$-LEEMQRRA-$NH_2$ | 1225.7 |
| 139. | $CH_3-(CH_2)_{20}-CO$-LEEMQRRA-$NH_2$ | 1353.8 |
| 140. | $CH_3-(CH_2)_4-CO$-LEEMQRRAD-$NH_2$ | 1326.7 |
| 141. | $CH_3-(CH_2)_6-CO$-LEEMQRRAD-$NH_2$ | 1354.7 |
| 142. | $CH_3-(CH_2)_8-CO$-LEEMQRRAD-$NH_2$ | 1382.8 |
| 143. | $CH_3-(CH_2)_{10}-CO$-LEEMQRRAD-$NH_2$ | 1410.8 |
| 144. | $CH_3-(CH_2)_{12}-CO$-LEEMQRRAD-$NH_2$ | 1438.9 |
| 145. | $CH_3-(CH_2)_{14}-CO$-LEEMQRRAD-$NH_2$ | 1466.9 |
| 146. | $CH_3-(CH_2)_{16}-CO$-LEEMQRRAD-$NH_2$ | 1495.0 |
| 147. | $CH_3-(CH_2)_{18}-CO$-LEEMQRRAD-$NH_2$ | 1423.0 |
| 148. | $CH_3-(CH_2)_{20}-CO$-LEEMQRRAD-$NH_2$ | 1551.1 |
| 149. | $CH_3-(CH_2)_4-CO$-LEEMQRRADQ-$NH_2$ | 1372.6 |
| 150. | $CH_3-(CH_2)_6-CO$-LEEMQRRADQ-$NH_2$ | 1400.6 |
| 151. | $CH_3-(CH_2)_8-CO$-LEEMQRRADQ-$NH_2$ | 1428.7 |
| 152. | $CH_3-(CH_2)_{10}-CO$-LEEMQRRADQ-$NH_2$ | 1456.7 |
| 153. | $CH_3-(CH_2)_{12}-CO$-LEEMQRRADQ-$NH_2$ | 1484.8 |
| 154. | $CH_3-(CH_2)_{14}-CO$-LEEMQRRADQ-$NH_2$ | 1512.8 |

-continued

| | Structure | Molecular weight |
|---|---|---|
| 155. | $CH_3-(CH_2)_{16}-CO$-LEEMQRRADQ-$NH_2$ | 1540.9 |
| 156. | $CH_3-(CH_2)_{18}-CO$-LEEMQRRADQ-$NH_2$ | 1468.9 |
| 157. | $CH_3-(CH_2)_{20}-CO$-LEEMQRRADQ-$NH_2$ | 1597.0 |
| 158. | $CH_3-(CH_2)_4-CO$-LEEMQRRADQL-$NH_2$ | 1485.8 |
| 159. | $CH_3-(CH_2)_6-CO$-LEEMQRRADQL-$NH_2$ | 1513.8 |
| 160. | $CH_3-(CH_2)_8-CO$-LEEMQRRADQL-$NH_2$ | 1541.9 |
| 161. | $CH_3-(CH_2)_{10}-CO$-LEEMQRRADQL-$NH_2$ | 1569.9 |
| 162. | $CH_3-(CH_2)_{12}-CO$-LEEMQRRADQL-$NH_2$ | 1598.0 |
| 163. | $CH_3-(CH_2)_{14}-CO$-LEEMQRRADQL-$NH_2$ | 1626.0 |
| 164. | $CH_3-(CH_2)_{16}-CO$-LEEMQRRADQL-$NH_2$ | 1654.1 |
| 165. | $CH_3-(CH_2)_{18}-CO$-LEEMQRRADQL-$NH_2$ | 1582.1 |
| 166. | $CH_3-(CH_2)_{20}-CO$-LEEMQRRADQL-$NH_2$ | 1710.2 |
| 167. | $CH_3-(CH_2)_4-CO$-MAEDADMRNELEEMQRRADQL-$NH_2$ | 2649.0 |
| 168. | $CH_3-(CH_2)_6-CO$-MAEDADMRNELEEMQRRADQL-$NH_2$ | 2677.0 |
| 169. | $CH_3-(CH_2)_8-CO$-MAEDADMRNELEEMQRRADQL-$NH_2$ | 2705.0 |
| 170. | $CH_3-(CH_2)_{10}-CO$-MAEDADMRNELEEMQRRADQL-$NH_2$ | 2733.1 |
| 171. | $CH_3-(CH_2)_{12}-CO$-MAEDADMRNELEEMQRRADQL-$NH_2$ | 2761.2 |
| 172. | $CH_3-(CH_2)_{14}-CO$-MAEDADMRNELEEMQRRADQL-$NH_2$ | 2789.2 |
| 173. | $CH_3-(CH_2)_{16}-CO$-MAEDADMRNELEEMQRRADQL-$NH_2$ | 2817.3 |
| 174. | $CH_3-(CH_2)_{18}-CO$-MAEDADMRNELEEMQRRADQL-$NH_2$ | 2745.3 |
| 175. | $CH_3-(CH_2)_{20}-CO$-MAEDADMRNELEEMQRRADQL-$NH_2$ | 2873.4 |
| 176. | $CH_3-(CH_2)_4-CO$-NQRATKMLGSG-$NH_2$ | 1259.5 |
| 177. | $CH_3-(CH_2)_6-CO$-NQRATKMLGSG-$NH_2$ | 1287.5 |
| 178. | $CH_3-(CH_2)_8-CO$-NQRATKMLGSG-$NH_2$ | 1315.6 |
| 179. | $CH_3-(CH_2)_{10}-CO$-NQRATKMLGSG-$NH_2$ | 1343.6 |
| 180. | $CH_3-(CH_2)_{12}-CO$-NQRATKMLGSG-$NH_2$ | 1371.7 |
| 181. | $CH_3-(CH_2)_{14}-CO$-NQRATKMLGSG-$NH_2$ | 1399.7 |
| 182. | $CH_3-(CH_2)_{16}-CO$-NQRATKMLGSG-$NH_2$ | 1427.8 |
| 183. | $CH_3-(CH_2)_{18}-CO$-NQRATKMLGSG-$NH_2$ | 1355.8 |
| 184. | $CH_3-(CH_2)_{20}-CO$-NQRATKMLGSG-$NH_2$ | 1483.9 |
| 185. | $CH_3-(CH_2)_4-CO$-QRATKMLGSG-$NH_2$ | 1145.4 |
| 186. | $CH_3-(CH_2)_6-CO$-QRATKMLGSG-$NH_2$ | 1173.4 |
| 187. | $CH_3-(CH_2)_8-CO$-QRATKMLGSG-$NH_2$ | 1201.5 |
| 188. | $CH_3-(CH_2)_{10}-CO$-QRATKMLGSG-$NH_2$ | 1229.5 |
| 189. | $CH_3-(CH_2)_{12}-CO$-QRATKMLGSG-$NH_2$ | 1257.6 |
| 190. | $CH_3-(CH_2)_{14}-CO$-QRATKMLGSG-$NH_2$ | 1285.6 |
| 191. | $CH_3-(CH_2)_{16}-CO$-QRATKMLGSG-$NH_2$ | 1313.7 |
| 192. | $CH_3-(CH_2)_{18}-CO$-QRATKMLGSG-$NH_2$ | 1241.7 |
| 193. | $CH_3-(CH_2)_{20}-CO$-QRATKMLGSG-$NH_2$ | 1369.8 |
| 194. | $CH_3-(CH_2)_4-CO$-SNKTRIDEANQRATKMLGSG-$NH_2$ | 2274.6 |
| 195. | $CH_3-(CH_2)_6-CO$-SNKTRIDEANQRATKMLGSG-$NH_2$ | 2302.6 |
| 196. | $CH_3-(CH_2)_8-CO$-SNKTRIDEANQRATKMLGSG-$NH_2$ | 2330.7 |
| 197. | $CH_3-(CH_2)_{10}-CO$-SNKTRIDEANQRATKMLGSG-$NH_2$ | 2358.7 |
| 198. | $CH_3-(CH_2)_{12}-CO$-SNKTRIDEANQRATKMLGSG-$NH_2$ | 2386.8 |
| 199. | $CH_3-(CH_2)_{14}-CO$-SNKTRIDEANQRATKMLGSG-$NH_2$ | 2414.8 |
| 200. | $CH_3-(CH_2)_{16}-CO$-SNKTRIDEANQRATKMLGSG-$NH_2$ | 2442.9 |
| 201. | $CH_3-(CH_2)_{18}-CO$-SNKTRIDEANQRATKMLGSG-$NH_2$ | 2370.9 |
| 202. | $CH_3-(CH_2)_{20}-CO$-SNKTRIDEANQRATKMLGSG-$NH_2$ | 2499.0 |
| 203. | $CH_3-(CH_2)_4-CO$-TRIDEANQRATKMLGSG-$NH_2$ | 1945.3 |
| 204. | $CH_3-(CH_2)_6-CO$-TRIDEANQRATKMLGSG-$NH_2$ | 1973.3 |
| 205. | $CH_3-(CH_2)_8-CO$-TRIDEANQRATKMLGSG-$NH_2$ | 2001.4 |
| 206. | $CH_3-(CH_2)_{10}-CO$-TRIDEANQRATKMLGSG-$NH_2$ | 2029.4 |
| 207. | $CH_3-(CH_2)_{12}-CO$-TRIDEANQRATKMLGSG-$NH_2$ | 2057.5 |
| 208. | $CH_3-(CH_2)_{14}-CO$-TRIDEANQRATKMLGSG-$NH_2$ | 2085.5 |
| 209. | $CH_3-(CH_2)_{16}-CO$-TRIDEANQRATKMLGSG-$NH_2$ | 2113.6 |
| 210. | $CH_3-(CH_2)_{18}-CO$-TRIDEANQRATKMLGSG-$NH_2$ | 2041.6 |
| 211. | $CH_3-(CH_2)_{20}-CO$-TRIDEANQRATKMLGSG-$NH_2$ | 2169.7 |
| 212. | $CH_3-(CH_2)_4-CO$-LESTRRMLQLVEE-$NH_2$ | 1701.0 |
| 213. | $CH_3-(CH_2)_6-CO$-LESTRRMLQLVEE-$NH_2$ | 1729.0 |
| 214. | $CH_3-(CH_2)_8-CO$-LESTRRMLQLVEE-$NH_2$ | 1757.1 |
| 215. | $CH_3-(CH_2)_{10}-CO$-LESTRRMLQLVEE-$NH_2$ | 1785.1 |
| 216. | $CH_3-(CH_2)_{12}-CO$-LESTRRMLQLVEE-$NH_2$ | 1813.2 |
| 217. | $CH_3-(CH_2)_{14}-CO$-LESTRRMLQLVEE-$NH_2$ | 1841.2 |
| 218. | $CH_3-(CH_2)_{16}-CO$-LESTRRMLQLVEE-$NH_2$ | 1869.3 |
| 219. | $CH_3-(CH_2)_{18}-CO$-LESTRRMLQLVEE-$NH_2$ | 1797.3 |
| 220. | $CH_3-(CH_2)_{20}-CO$-LESTRRMLQLVEE-$NH_2$ | 1925.4 |
| 221. | $CH_3-(CH_2)_4-CO$-NKDMKEAEKNLT-$NH_2$ | 1517.8 |
| 222. | $CH_3-(CH_2)_6-CO$-NKDMKEAEKNLT-$NH_2$ | 1545.8 |
| 223. | $CH_3-(CH_2)_8-CO$-NKDMKEAEKNLT-$NH_2$ | 1573.9 |
| 224. | $CH_3-(CH_2)_{10}-CO$-NKDMKEAEKNLT-$NH_2$ | 1601.9 |
| 225. | $CH_3-(CH_2)_{12}-CO$-NKDMKEAEKNLT-$NH_2$ | 1630.0 |
| 226. | $CH_3-(CH_2)_{14}-CO$-NKDMKEAEKNLT-$NH_2$ | 1658.0 |
| 227. | $CH_3-(CH_2)_{16}-CO$-NKDMKEAEKNLT-$NH_2$ | 1686.1 |
| 228. | $CH_3-(CH_2)_{18}-CO$-NKDMKEAEKNLT-$NH_2$ | 1614.1 |
| 229. | $CH_3-(CH_2)_{20}-CO$-NKDMKEAEKNLT-$NH_2$ | 1742.2 |
| 230. | $CH_3-(CH_2)_4-CO$-IMEKADSNKTRIDEANQRATKMLGSG-$NH_2$ | 2962.4 |

| | Structure | Molecular weight |
|---|---|---|
| 231. | CH$_3$—(CH$_2$)$_6$—CO-IMEKADSNKTRIDEANQRATKMLGSG-NH$_2$ | 2990.4 |
| 232. | CH$_3$—(CH$_2$)$_8$—CO-IMEKADSNKTRIDEANQRATKMLGSG-NH$_2$ | 3018.5 |
| 233. | CH$_3$—(CH$_2$)$_{10}$—CO-IMEKADSNKTRIDEANQRATKMLGSG-NH$_2$ | 3046.5 |
| 234. | CH$_3$—(CH$_2$)$_{12}$—CO-IMEKADSNKTRIDEANQRATKMLGSG-NH$_2$ | 3074.6 |
| 235. | CH$_3$—(CH$_2$)$_{14}$—CO-IMEKADSNKTRIDEANQRATKMLGSG-NH$_2$ | 3102.6 |
| 236. | CH$_3$—(CH$_2$)$_{16}$—CO-IMEKADSNKTRIDEANQRATKMLGSG-NH$_2$ | 3130.7 |
| 237. | CH$_3$—(CH$_2$)$_{18}$—CO-IMEKADSNKTRIDEANQRATKMLGSG-NH$_2$ | 3058.7 |
| 238. | CH$_3$—(CH$_2$)$_{20}$—CO-IMEKADSNKTRIDEANQRATKMLGSG-NH$_2$ | 3186.8 |
| 239. | Ac-EEMQRR-NH—(CH$_2$)$_5$—CH$_3$ | 973.1 |
| 240. | Ac-EEMQRR-NH—(CH$_2$)$_7$—CH$_3$ | 1001.1 |
| 241. | Ac-EEMQRR-NH—(CH$_2$)$_9$—CH$_3$ | 1029.2 |
| 242. | Ac-EEMQRR-NH—(CH$_2$)$_{13}$—CH$_3$ | 1085.3 |
| 243. | Ac-EEMQRR-NH—(CH$_2$)$_{17}$—CH$_3$ | 1141.4 |
| 244. | Ac-EEMQRRA-NH—(CH$_2$)$_5$—CH$_3$ | 1044.4 |
| 245. | Ac-EEMQRRA-NH—(CH$_2$)$_7$—CH$_3$ | 1072.4 |
| 246. | Ac-EEMQRRA-NH—(CH$_2$)$_9$—CH3 | 1100.5 |
| 247. | Ac-EEMQRRA-NH—(CH$_2$)$_{11}$—CH$_3$ | 1128.6 |
| 248. | Ac-EEMQRRA-NH—(CH$_2$)$_{13}$—CH$_3$ | 1156.6 |
| 249. | Ac-EEMQRRA-NH—(CH$_2$)$_{15}$CH$_3$ | 1184.7 |
| 250. | Ac-EEMQRRA-NH—(CH$_2$)$_{17}$—CH$_3$ | 1212.7 |
| 251. | Ac-EEMQRRAD-NH—(CH$_2$)$_5$—CH$_3$ | 1159.3 |
| 252. | Ac-EEMQRRAD-NH—(CH$_2$)$_7$—CH$_3$ | 1187.3 |
| 253. | Ac-EEMQRRAD-NH—(CH$_2$)$_9$—CH$_3$ | 1215.4 |
| 254. | Ac-EEMQRRAD-NH—(CH$_2$)$_{11}$—CH$_3$ | 1243.5 |
| 255. | Ac-EEMQRRAD-NH—(CH$_2$)$_{13}$—CH$_3$ | 1271.5 |
| 256. | Ac-EEMQRRAD-NH—(CH$_2$)$_{15}$—CH$_3$ | 1299.6 |
| 257. | Ac-EEMQRRAD-NH—(CH$_2$)$_{17}$—CH$_3$ | 1327.6 |
| 258. | Ac-ELEEMQRRADQLA-NH—(CH$_2$)$_5$—CH$_3$ | 1713.9 |
| 259. | Ac-ELEEMQRRADQLA-NH—(CH$_2$)$_7$—CH$_3$ | 1741.9 |
| 260. | Ac-ELEEMQRRADQLA-NH—(CH$_2$)$_9$—CH$_3$ | 1770.0 |
| 261. | Ac-ELEEMQRRADQLA-NH—(CH$_2$)$_{11}$—CH$_3$ | 1798.1 |
| 262. | Ac-ELEEMQRRADQLA-NH—(CH$_2$)$_{13}$—CH$_3$ | 1826.1 |
| 263. | Ac-ELEEMQRRADQLA-NH—(CH$_2$)$_{15}$—CH$_3$ | 1854.2 |
| 264. | Ac-ELEEMQRRADQLA-NH—(CH$_2$)$_{17}$—CH$_3$ | 1882.2 |
| 265. | Ac-ADESLESTRRMLQLVEESKDAGI-NH—(CH$_2$)$_5$—CH$_3$ | 2660.0 |
| 266. | Ac-ADESLESTRRMLQLVEESKDAGI-NH—(CH$_2$)$_7$—CH$_3$ | 2688.0 |
| 267. | Ac-ADESLESTRRMLQLVEESKDAGI-NH—(CH$_2$)$_9$—CH$_3$ | 2716.1 |
| 268. | Ac-ADESLESTRRMLQLVEESKDAGI-NH—(CH$_2$)$_{11}$—CH$_3$ | 2744.2 |
| 269. | Ac-ADESLESTRRMLQLVEESKDAGI-NH—(CH$_2$)$_{13}$—CH$_3$ | 2772.2 |
| 270. | Ac-ADESLESTRRMLQLVEESKDAGI-NH—(CH$_2$)$_{15}$—CH$_3$ | 2800.3 |
| 271. | Ac-ADESLESTRRMLQLVEESKDAGI-NH—(CH$_2$)$_{17}$—CH$_3$ | 2828.3 |
| 272. | Ac-DEANQRATKMLGSG-NH—(CH$_2$)$_5$—CH$_3$ | 1559.8 |
| 273. | Ac-DEANQRATKMLGSG-NH—(CH$_2$)$_7$—CH$_3$ | 1587.8 |
| 274. | Ac-DEANQRATKMLGSG-NH—(CH$_2$)$_9$—CH$_3$ | 1615.9 |
| 275. | Ac-DEANQRATKMLGSG-NH—(CH$_2$)$_{11}$—CH$_3$ | 1644.0 |
| 276. | Ac-DEANQRATKMLGSG-NH—(CH$_2$)$_{13}$—CH$_3$ | 1672.0 |
| 277. | Ac-DEANQRATKMLGSG-NH—(CH$_2$)$_{15}$—CH$_3$ | 1700.1 |
| 278. | Ac-DEANQRATKMLGSG-NH—(CH$_2$)$_{17}$—CH$_3$ | 1728.1 |
| 279. | Ac-EEMQRRADQ-NH—(CH$_2$)$_5$—CH$_3$ | 1244.4 |
| 280. | Ac-EEMQRRADQ-NH—(CH$_2$)$_7$—CH$_3$ | 1272.4 |
| 281. | Ac-EEMQRRADQ-NH—(CH$_2$)$_9$—CH$_3$ | 1300.5 |
| 282. | Ac-EEMQRRADQ-NH—(CH$_2$)$_{11}$—CH$_3$ | 1328.6 |
| 283. | Ac-EEMQRRADQ-NH—(CH$_2$)$_{13}$—CH$_3$ | 1356.6 |
| 284. | Ac-EEMQRRADQ-NH—(CH$_2$)$_{15}$—CH$_3$ | 1384.7 |
| 285. | Ac-EEMQRRADQ-NH—(CH$_2$)$_{17}$—CH$_3$ | 1412.7 |
| 286. | Ac-EEMQRRADQL-NH—(CH$_2$)$_5$—CH$_3$ | 1357.6 |
| 287. | Ac-EEMQRRADQL-NH—(CH$_2$)$_7$—CH$_3$ | 1385.6 |
| 288. | Ac-EEMQRRADQL-NH—(CH$_2$)$_9$—CH$_3$ | 1413.7 |
| 289. | Ac-EEMQRRADQL-NH—(CH$_2$)$_{11}$—CH$_3$ | 1441.8 |
| 290. | Ac-EEMQRRADQL-NH—(CH$_2$)$_{13}$—CH$_3$ | 1469.8 |
| 291. | Ac-EEMQRRADQL-NH—(CH$_2$)$_{15}$—CH$_3$ | 1497.9 |
| 292. | Ac-EEMQRRADQL-NH—(CH$_2$)$_{17}$—CH$_3$ | 1525.9 |
| 293. | Ac-ELEEMQRR-NH—(CH$_2$)$_5$—CH$_3$ | 1172.4 |
| 294. | Ac-ELEEMQRR-NH—(CH$_2$)$_7$—CH$_3$ | 1200.4 |
| 295. | Ac-ELEEMQRR-NH—(CH$_2$)$_9$—CH$_3$ | 1228.5 |
| 296. | Ac-ELEEMQRR-NH—(CH$_2$)$_{11}$—CH$_3$ | 1256.6 |
| 297. | Ac-ELEEMQRR-NH—(CH$_2$)$_{13}$—CH$_3$ | 1284.6 |
| 298. | Ac-ELEEMQRR-NH—(CH$_2$)$_{15}$—CH$_3$ | 1312.7 |
| 299. | Ac-ELEEMQRR-NH—(CH$_2$)$_{17}$—CH$_3$ | 1340.7 |
| 300. | Ac-ELEEMQRRA-NH—(CH$_2$)$_5$—CH$_3$ | 1243.5 |
| 301. | Ac-ELEEMQRRA-NH—(CH$_2$)$_7$—CH$_3$ | 1271.5 |
| 302. | Ac-ELEEMQRRA-NH—(CH$_2$)$_9$—CH$_3$ | 1299.6 |
| 303. | Ac-ELEEMQRRA-NH—(CH$_2$)$_{11}$—CH$_3$ | 1327.7 |
| 304. | Ac-ELEEMQRRA-NH—(CH$_2$)$_{13}$—CH$_3$ | 1355.7 |
| 305. | Ac-ELEEMQRRA-NH—(CH$_2$)$_{15}$—CH$_3$ | 1383.8 |
| 306. | Ac-ELEEMQRRA-NH—(CH$_2$)$_{17}$—CH$_3$ | 1411.8 |

-continued

| Structure | Molecular weight |
|---|---|
| 307. Ac-ELEEMQRRAD-NH—(CH$_2$)$_5$—CH$_3$ | 1358.6 |
| 308. Ac-ELEEMQRRAD-NH—(CH$_2$)$_7$—CH$_3$ | 1386.6 |
| 309. Ac-ELEEMQRRAD-NH—(CH$_2$)$_9$—CH$_3$ | 1414.7 |
| 310. Ac-ELEEMQRRAD-NH—(CH$_2$)$_{11}$—CH$_3$ | 1442.8 |
| 311. Ac-ELEEMQRRAD-NH—(CH$_2$)$_{13}$—CH$_3$ | 1470.8 |
| 312. Ac-ELEEMQRRAD-NH—(CH$_2$)$_{15}$—CH$_3$ | 1498.9 |
| 313. Ac-ELEEMQRRAD-NH—(CH$_2$)$_{17}$—CH$_3$ | 1526.9 |
| 314. Ac-ELEEMQRRADQ-NH—(CH$_2$)$_5$—CH$_3$ | 1486.7 |
| 315. Ac-ELEEMQRRADQ-NH—(CH$_2$)$_7$—CH$_3$ | 1514.7 |
| 316. Ac-ELEEMQRRADQ-NH—(CH$_2$)$_9$—CH$_3$ | 1542.8 |
| 317. Ac-ELEEMQRRADQ-NH—(CH$_2$)$_{11}$—CH$_3$ | 1570.9 |
| 318. Ac-ELEEMQRRADQ-NH—(CH$_2$)$_{13}$—CH$_3$ | 1598.9 |
| 319. Ac-ELEEMQRRADQ-NH—(CH$_2$)$_{15}$—CH$_3$ | 1627.0 |
| 320. Ac-ELEEMQRRADQ-NH—(CH$_2$)$_{17}$—CH$_3$ | 1655.0 |
| 321. Ac-ELEEMQRRADQL-NH—(CH$_2$)$_5$—CH$_3$ | 1599.9 |
| 322. Ac-ELEEMQRRADQL-NH—(CH$_2$)$_7$—CH$_3$ | 1627.9 |
| 323. Ac-ELEEMQRRADQL-NH—(CH$_2$)$_9$—CH$_3$ | 1656.0 |
| 324. Ac-ELEEMQRRADQL-NH—(CH$_2$)$_{11}$—CH$_3$ | 1684.1 |
| 325. Ac-ELEEMQRRADQL-NH—(CH$_2$)$_{13}$—CH$_3$ | 1712.1 |
| 326. Ac-ELEEMQRRADQL-NH—(CH$_2$)$_{15}$—CH$_3$ | 1740.2 |
| 327. Ac-ELEEMQRRADQL-NH—(CH$_2$)$_{17}$—CH$_3$ | 1768.2 |
| 328. Ac-KNLTDL-NH—(CH$_2$)$_5$—CH$_3$ | 785.0 |
| 329. Ac-KNLTDL-NH—(CH$_2$)$_7$—CH$_3$ | 813.0 |
| 330. Ac-KNLTDL-NH—(CH$_2$)$_9$—CH$_3$ | 841.1 |
| 331. Ac-KNLTDL-NH—(CH$_2$)$_{11}$—CH$_3$ | 869.2 |
| 332. Ac-KNLTDL-NH—(CH$_2$)$_{13}$—CH$_3$ | 897.2 |
| 333. Ac-KNLTDL-NH—(CH$_2$)$_{15}$—CH$_3$ | 925.3 |
| 334. Ac-KNLTDL-NH—(CH$_2$)$_{17}$—CH$_3$ | 953.3 |
| 335. Ac-LEEMQRR-NH—(CH$_2$)$_5$—CH$_3$ | 1043.3 |
| 336. Ac-LEEMQRR-NH—(CH$_2$)$_7$—CH$_3$ | 1071.3 |
| 337. Ac-LEEMQRR-NH—(CH$_2$)$_9$—CH$_3$ | 1099.4 |
| 338. Ac-LEEMQRR-NH—(CH$_2$)$_{11}$—CH$_3$ | 1127.5 |
| 339. Ac-LEEMQRR-NH—(CH$_2$)$_{13}$—CH$_3$ | 1155.5 |
| 340. Ac-LEEMQRR-NH—(CH$_2$)$_{15}$—CH$_3$ | 1183.6 |
| 341. Ac-LEEMQRR-NH—(CH$_2$)$_{17}$—CH$_3$ | 1211.6 |
| 342. Ac-LEEMQRRA-NH—(CH$_2$)$_5$—CH$_3$ | 1114.4 |
| 343. Ac-LEEMQRRA-NH—(CH$_2$)$_7$—CH$_3$ | 1142.4 |
| 344. Ac-LEEMQRRA-NH—(CH$_2$)$_9$—CH$_3$ | 1170.5 |
| 345. Ac-LEEMQRRA-NH—(CH$_2$)$_{11}$—CH$_3$ | 1198.6 |
| 346. Ac-LEEMQRRA-NH—(CH$_2$)$_{13}$—CH$_3$ | 1226.6 |
| 347. Ac-LEEMQRRA-NH—(CH$_2$)$_{15}$—CH$_3$ | 1254.7 |
| 348. Ac-LEEMQRRA-NH—(CH$_2$)$_{17}$—CH$_3$ | 1282.7 |
| 349. Ac-LEEMQRRAD-NH—(CH$_2$)$_5$—CH$_3$ | 1229.5 |
| 350. Ac-LEEMQRRAD-NH—(CH$_2$)$_7$—CH$_3$ | 1257.5 |
| 351. Ac-LEEMQRRAD-NH—(CH$_2$)$_9$—CH$_3$ | 1285.6 |
| 352. Ac-LEEMQRRAD-NH—(CH$_2$)$_{11}$—CH$_3$ | 1313.7 |
| 353. Ac-LEEMQRRAD-NH—(CH$_2$)$_{13}$—CH$_3$ | 1341.7 |
| 354. Ac-LEEMQRRAD-NH—(CH$_2$)$_{15}$—CH$_3$ | 1369.8 |
| 355. Ac-LEEMQRRAD-NH—(CH$_2$)$_{17}$—CH$_3$ | 1397.8 |
| 356. Ac-LEEMQRRADQ-NH—(CH$_2$)$_5$—CH$_3$ | 1357.6 |
| 357. Ac-LEEMQRRADQ-NH—(CH$_2$)$_7$—CH$_3$ | 1385.6 |
| 358. Ac-LEEMQRRADQ-NH—(CH$_2$)$_9$—CH$_3$ | 1413.7 |
| 359. Ac-LEEMQRRADQ-NH—(CH$_2$)$_{11}$—CH$_3$ | 1441.8 |
| 360. Ac-LEEMQRRADQ-NH—(CH$_2$)$_{13}$—CH$_3$ | 1469.8 |
| 361. Ac-LEEMQRRADQ-NH—(CH$_2$)$_{15}$—CH$_3$ | 1497.9 |
| 362. Ac-LEEMQRRADQ-NH—(CH$_2$)$_{17}$—CH$_3$ | 1525.9 |
| 363. Ac-LEEMQRRADQL-NH—(CH$_2$)$_5$—CH$_3$ | 1470.8 |
| 364. Ac-LEEMQRRADQL-NH—(CH$_2$)$_7$—CH$_3$ | 1498.8 |
| 365. Ac-LEEMQRRADQL-NH—(CH$_2$)$_9$—CH$_3$ | 1526.9 |
| 366. Ac-LEEMQRRADQL-NH—(CH$_2$)$_{11}$—CH$_3$ | 1555.0 |
| 367. Ac-LEEMQRRADQL-NH—(CH$_2$)$_{13}$—CH$_3$ | 1583.0 |
| 368. Ac-LEEMQRRADQL-NH—(CH$_2$)$_{15}$—CH$_3$ | 1611.1 |
| 369. Ac-LEEMQRRADQL-NH—(CH$_2$)$_{17}$—CH$_3$ | 1639.1 |
| 370. Ac-MAEDADMRNELEEMQRRADQL-NH—(CH$_2$)$_5$—CH$_3$ | 2634.0 |
| 371. Ac-MAEDADMRNELEEMQRRADQL-NH—(CH$_2$)$_7$—CH$_3$ | 2662.0 |
| 372. Ac-MAEDADMRNELEEMQRRADQL-NH—(CH$_2$)$_9$—CH$_3$ | 2690.1 |
| 373. Ac-MAEDADMRNELEEMQRRADQL-NH—(CH$_2$)$_{11}$—CH$_3$ | 2718.2 |
| 374. Ac-MAEDADMRNELEEMQRRADQL-NH—(CH$_2$)$_{13}$—CH$_3$ | 2746.2 |
| 375. Ac-MAEDADMRNELEEMQRRADQL-NH—(CH$_2$)$_{15}$—CH$_3$ | 2774.3 |
| 376. Ac-MAEDADMRNELEEMQRRADQL-NH—(CH$_2$)$_{17}$—CH$_3$ | 2802.3 |
| 377. Ac-NQRATKMLGSG-NH—(CH$_2$)$_5$—CH$_3$ | 1244.5 |
| 378. Ac-NQRATKMLGSG-NH—(CH$_2$)$_7$—CH$_3$ | 1272.5 |
| 379. Ac-NQRATKMLGSG-NH—(CH$_2$)$_9$—CH$_3$ | 1300.6 |
| 380. Ac-NQRATKMLGSG-NH—(CH$_2$)$_{11}$—CH$_3$ | 1328.7 |
| 381. Ac-NQRATKMLGSG-NH—(CH$_2$)$_{13}$—CH$_3$ | 1356.7 |
| 382. Ac-NQRATKMLGSG-NH—(CH$_2$)$_{15}$—CH$_3$ | 1384.8 |

-continued

| | Structure | Molecular weight |
|---|---|---|
| 383. | Ac-NQRATKMLGSG-NH—$(CH_2)_{17}$—$CH_3$ | 1412.8 |
| 384. | Ac-QRATKMLGSG-NH—$(CH_2)_5$—$CH_3$ | 1130.4 |
| 385. | Ac-QRATKMLGSG-NH—$(CH_2)_7$—$CH_3$ | 1158.4 |
| 386. | Ac-QRATKMLGSG-NH—$(CH_2)_9$—$CH_3$ | 1186.5 |
| 387. | Ac-QRATKMLGSG-NH—$(CH_2)_{11}$—$CH_3$ | 1214.6 |
| 388. | Ac-QRATKMLGSG-NH—$(CH_2)_{13}$—$CH_3$ | 1242.6 |
| 389. | Ac-QRATKMLGSG-NH—$(CH_2)_{15}$—$CH_3$ | 1270.7 |
| 390. | Ac-QRATKMLGSG-NH—$(CH_2)_{17}$—$CH_3$ | 1298.7 |
| 391. | Ac-SNKTRIDEANQRATKMLGSG-NH—$(CH_2)_5$—$CH_3$ | 2259.6 |
| 392. | Ac-SNKTRIDEANQRATKMLGSG-NH—$(CH_2)_7$—$CH_3$ | 2287.6 |
| 393. | Ac-SNKTRIDEANQRATKMLGSG-NH—$(CH_2)_9$—$CH_3$ | 2315.7 |
| 394. | Ac-SNKTRIDEANQRATKMLGSG-NH—$(CH_2)_{11}$—$CH_3$ | 2343.8 |
| 395. | Ac-SNKTRIDEANQRATKMLGSG-NH—$(CH_2)_{13}$—$CH_3$ | 2371.8 |
| 396. | Ac-SNKTRIDEANQRATKMLGSG-NH—$(CH_2)_{15}$—$CH_3$ | 2399.9 |
| 397. | Ac-SNKTRIDEANQRATKMLGSG-NH—$(CH_2)_{17}$—$CH_3$ | 2427.9 |
| 398. | Ac-TRIDEANQRATKMLGSG-NH—$(CH_2)_5$—$CH_3$ | 1930.3 |
| 399. | Ac-TRIDEANQRATKMLGSG-NH—$(CH_2)_7$—$CH_3$ | 1958.3 |
| 400. | Ac-TRIDEANQRATKMLGSG-NH—$(CH_2)_9$—$CH_3$ | 1986.4 |
| 401. | Ac-TRIDEANQRATKMLGSG-NH—$(CH_2)_{11}$—$CH_3$ | 2014.5 |
| 402. | Ac-TRIDEANQRATKMLGSG-NH—$(CH_2)_{13}$—$CH_3$ | 2042.5 |
| 403. | Ac-TRIDEANQRATKMLGSG-NH—$(CH_2)_{15}$—$CH_3$ | 2070.6 |
| 404. | Ac-TRIDEANQRATKMLGSG-NH—$(CH_2)_{17}$—$CH_3$ | 2098.6 |
| 405. | Ac-LESTRRMLQLVEE-NH—$(CH_2)_5$—$CH_3$ | 1729.0 |
| 406. | Ac-LESTRRMLQLVEE-NH—$(CH_2)_7$—$CH_3$ | 1757.0 |
| 407. | Ac-LESTRRMLQLVEE-NH—$(CH_2)_9$—$CH_3$ | 1785.1 |
| 408. | Ac-LESTRRMLQLVEE-NH—$(CH_2)_{11}$—$CH_3$ | 1813.2 |
| 409. | Ac-LESTRRMLQLVEE-NH—$(CH_2)_{13}$—$CH_3$ | 1841.2 |
| 410. | Ac-LESTRRMLQLVEE-NH—$(CH_2)_{15}$—$CH_3$ | 1869.3 |
| 411. | Ac-LESTRRMLQLVEE-NH—$(CH_2)_{17}$—$CH_3$ | 1897.3 |
| 412. | Ac-NKDMKEAEKNLT-NH—$(CH_2)_5$—$CH_3$ | 1545.8 |
| 413. | Ac-NKDMKEAEKNLT-NH—$(CH_2)_7$—$CH_3$ | 1573.8 |
| 414. | Ac-NKDMKEAEKNLT-NH—$(CH_2)_9$—$CH_3$ | 1601.9 |
| 415. | Ac-NKDMKEAEKNLT-NH—$(CH_2)_{11}$—$CH_3$ | 1630.0 |
| 416. | Ac-NKDMKEAEKNLT-NH—$(CH_2)_{13}$—$CH_3$ | 1658.0 |
| 417. | Ac-NKDMKEAEKNLT-NH—$(CH_2)_{15}$—$CH_3$ | 1686.1 |
| 418. | Ac-NKDMKEAEKNLT-NH—$(CH_2)_{17}$—$CH_3$ | 1714.1 |
| 419. | Ac-IMEKADSNKTRIDEANQRATKMLGSG-NH—$(CH_2)_5$—$CH_3$ | 2990.4 |
| 420. | Ac-IMEKADSNKTRIDEANQRATKMLGSG-NH—$(CH_2)_7$—$CH_3$ | 3018.4 |
| 421. | Ac-IMEKADSNKTRIDEANQRATKMLGSG-NH—$(CH_2)_9$—$CH_3$ | 3046.5 |
| 422. | Ac-IMEKADSNKTRIDEANQRATKMLGSG-NH—$(CH_2)_{11}$—$CH_3$ | 3074.6 |
| 423. | Ac-IMEKADSNKTRIDEANQRATKMLGSG-NH—$(CH_2)_{13}$—$CH_3$ | 3102.6 |
| 424. | Ac-IMEKADSNKTRIDEANQRATKMLGSG-NH—$(CH_2)_{15}$—$CH_3$ | 3130.7 |
| 425. | Ac-IMEKADSNKTRIDEANQRATKMLGSG-NH—$(CH_2)_{17}$—$CH_3$ | 3158.7 |
| 426. | Ac-$PEG_1$-EEMQRRA-$NH_2$ | 1262.6 |
| 427. | Ac-$PEG_2$-EEMQRRA-$NH_2$ | 1565.0 |
| 428. | Ac-$PEG_3$-EEMQRRA-$NH_2$ | 1867.4 |
| 429. | Ac-$PEG_4$-EEMQRRA-$NH_2$ | 2169.7 |
| 430. | Ac-$PEG_5$-EEMQRRA-$NH_2$ | 2472.1 |
| 431. | Ac-$PEG_1$-EEMQRRAD-$NH_2$ | 1377.5 |
| 432. | Ac-$PEG_2$-EEMQRRAD-$NH_2$ | 1679.9 |
| 433. | Ac-$PEG_3$-EEMQRRAD-$NH_2$ | 1982.3 |
| 434. | Ac-$PEG_4$-EEMQRRAD-$NH_2$ | 2284.6 |
| 435. | Ac-$PEG_5$-EEMQRRAD-$NH_2$ | 2587.0 |
| 436. | Ac-$PEG_1$-ELEEMQRRADQLA-$NH_2$ | 1932.1 |
| 437. | Ac-$PEG_2$-ELEEMQRRADQLA-$NH_2$ | 2234.5 |
| 438. | Ac-$PEG_3$-ELEEMQRRADQLA-$NH_2$ | 2536.9 |
| 439. | Ac-$PEG_4$-ELEEMQRRADQLA-$NH_2$ | 2839.2 |
| 440. | Ac-$PEG_5$-ELEEMQRRADQLA-$NH_2$ | 3141.6 |
| 441. | Ac-$PEG_1$-ADESLESTRRMLQLVEESKDAGI-$NH_2$ | 2921.2 |
| 442. | Ac-$PEG_2$-ADESLESTRRMLQLVEESKDAGI-$NH_2$ | 3223.6 |
| 443. | Ac-$PEG_3$-ADESLESTRRMLQLVEESKDAGI-$NH_2$ | 3526.0 |
| 444. | Ac-$PEG_4$-ADESLESTRRMLQLVEESKDAGI-$NH_2$ | 3828.3 |
| 445. | Ac-$PEG_5$-ADESLESTRRMLQLVEESKDAGI-$NH_2$ | 4130.7 |
| 446. | Ac-$PEG_1$-DEANQRATKMLGSG-$NH_2$ | 1821.0 |
| 447. | Ac-$PEG_2$-DEANQRATKMLGSG-$NH_2$ | 2123.4 |
| 448. | Ac-$PEG_3$-DEANQRATKMLGSG-$NH_2$ | 2425.8 |
| 449. | Ac-$PEG_4$-DEANQRATKMLGSG-$NH_2$ | 2728.1 |
| 450. | Ac-$PEG_5$-DEANQRATKMLGSG-$NH_2$ | 3030.5 |
| 451. | Ac-$PEG_1$-EEMQRRADQ-$NH_2$ | 1505.6 |
| 452. | Ac-$PEG_2$-EEMQRRADQ-$NH_2$ | 1808.0 |
| 453. | Ac-$PEG_3$-EEMQRRADQ-$NH_2$ | 2110.4 |
| 454. | Ac-$PEG_4$-EEMQRRADQ-$NH_2$ | 2412.7 |
| 455. | Ac-$PEG_5$-EEMQRRADQ-$NH_2$ | 2715.1 |
| 456. | Ac-$PEG_1$-EEMQRRADQL-$NH_2$ | 1618.8 |
| 457. | Ac-$PEG_2$-EEMQRRADQL-$NH_2$ | 1921.2 |
| 458. | Ac-$PEG_3$-EEMQRRADQL-$NH_2$ | 2223.6 |

| | Structure | Molecular weight |
|---|---|---|
| 459. | Ac-PEG$_4$-EEMQRRADQL-NH$_2$ | 2525.9 |
| 460. | Ac-PEG$_5$-EEMQRRADQL-NH$_2$ | 2828.3 |
| 461. | Ac-PEG$_1$-ELEEMQRR-NH$_2$ | 1433.6 |
| 462. | Ac-PEG$_2$-ELEEMQRR-NH$_2$ | 1736.0 |
| 463. | Ac-PEG$_3$-ELEEMQRR-NH$_2$ | 2038.4 |
| 464. | Ac-PEG$_4$-ELEEMQRR-NH$_2$ | 2340.7 |
| 465. | Ac-PEG$_5$-ELEEMQRR-NH$_2$ | 2643.1 |
| 466. | Ac-PEG$_1$-ELEEMQRRA-NH$_2$ | 1504.7 |
| 467. | Ac-PEG$_2$-ELEEMQRRA-NH$_2$ | 1807.1 |
| 468. | Ac-PEG$_3$-ELEEMQRRA-NH$_2$ | 2109.5 |
| 469. | Ac-PEG$_4$-ELEEMQRRA-NH$_2$ | 2411.8 |
| 470. | Ac-PEG$_5$-ELEEMQRRA-NH$_2$ | 2714.2 |
| 471. | Ac-PEG$_1$-ELEEMQRRAD-NH$_2$ | 1619.8 |
| 472. | Ac-PEG$_2$-ELEEMQRRAD-NH$_2$ | 1922.2 |
| 473. | Ac-PEG$_3$-ELEEMQRRAD-NH$_2$ | 2224.6 |
| 474. | Ac-PEG$_4$-ELEEMQRRAD-NH$_2$ | 2526.9 |
| 475. | Ac-PEG$_5$-ELEEMQRRAD-NH$_2$ | 2829.3 |
| 476. | Ac-PEG$_1$-ELEEMQRRADQ-NH$_2$ | 1747.9 |
| 477. | Ac-PEG$_2$-ELEEMQRRADQ-NH$_2$ | 2050.3 |
| 478. | Ac-PEG$_3$-ELEEMQRRADQ-NH$_2$ | 2352.7 |
| 479. | Ac-PEG$_4$-ELEEMQRRADQ-NH$_2$ | 2655.0 |
| 480. | Ac-PEG$_5$-ELEEMQRRADQ-NH$_2$ | 2957.4 |
| 481. | Ac-PEG$_1$-ELEEMQRRADQL-NH$_2$ | 1861.1 |
| 482. | Ac-PEG$_2$-ELEEMQRRADQL-NH$_2$ | 2163.5 |
| 483. | Ac-PEG$_3$-ELEEMQRRADQL-NH$_2$ | 2465.9 |
| 484. | Ac-PEG$_4$-ELEEMQRRADQL-NH$_2$ | 2768.2 |
| 485. | Ac-PEG$_5$-ELEEMQRRADQL-NH$_2$ | 3070.6 |
| 486. | Ac-PEG$_1$-KNLTDL-NH$_2$ | 1046.2 |
| 487. | Ac-PEG$_2$-KNLTDL-NH$_2$ | 1348.6 |
| 488. | Ac-PEG$_3$-KNLTDL-NH$_2$ | 1651.0 |
| 489. | Ac-PEG$_4$-KNLTDL-NH$_2$ | 1953.3 |
| 490. | Ac-PEG$_5$-KNLTDL-NH$_2$ | 2255.7 |
| 491. | Ac-PEG$_1$-LEEMQRR-NH$_2$ | 1304.5 |
| 492. | Ac-PEG$_2$-LEEMQRR-NH$_2$ | 1606.9 |
| 493. | Ac-PEG$_3$-LEEMQRR-NH$_2$ | 1909.3 |
| 494. | Ac-PEG$_4$-LEEMQRR-NH$_2$ | 2211.6 |
| 495. | Ac-PEG$_5$-LEEMQRR-NH$_2$ | 2514.0 |
| 496. | Ac-PEG$_1$-LEEMQRRA-NH$_2$ | 1375.6 |
| 497. | Ac-PEG$_2$-LEEMQRRA-NH$_2$ | 1678.0 |
| 498. | Ac-PEG$_3$-LEEMQRRA-NH$_2$ | 1980.4 |
| 499. | Ac-PEG$_4$-LEEMQRRA-NH$_2$ | 2282.7 |
| 500. | Ac-PEG$_5$-LEEMQRRA-NH$_2$ | 2585.1 |
| 501. | Ac-PEG$_1$-LEEMQRRAD-NH$_2$ | 1572.9 |
| 502. | Ac-PEG$_2$-LEEMQRRAD-NH$_2$ | 1875.3 |
| 503. | Ac-PEG$_3$-LEEMQRRAD-NH$_2$ | 2177.7 |
| 504. | Ac-PEG$_4$-LEEMQRRAD-NH$_2$ | 2480.0 |
| 505. | Ac-PEG$_5$-LEEMQRRAD-NH$_2$ | 2782.4 |
| 506. | Ac-PEG$_1$-LEEMQRRADQ-NH$_2$ | 1618.8 |
| 507. | Ac-PEG$_2$-LEEMQRRADQ-NH$_2$ | 1921.2 |
| 508. | Ac-PEG$_3$-LEEMQRRADQ-NH$_2$ | 2223.6 |
| 509. | Ac-PEG$_4$-LEEMQRRADQ-NH$_2$ | 2525.9 |
| 510. | Ac-PEG$_5$-LEEMQRRADQ-NH$_2$ | 2828.3 |
| 511. | Ac-PEG$_1$-LEEMQRRADQL-NH$_2$ | 1732.0 |
| 512. | Ac-PEG$_2$-LEEMQRRADQL-NH$_2$ | 2034.4 |
| 513. | Ac-PEG$_3$-LEEMQRRADQL-NH$_2$ | 2336.8 |
| 514. | Ac-PEG$_4$-LEEMQRRADQL-NH$_2$ | 2639.1 |
| 515. | Ac-PEG$_5$-LEEMQRRADQL-NH$_2$ | 2941.5 |
| 516. | Ac-PEG$_1$-MAEDADMRNELEEMQRRADQL-NH$_2$ | 2895.2 |
| 517. | Ac-PEG$_2$-MAEDADMRNELEEMQRRADQL-NH$_2$ | 3197.6 |
| 518. | Ac-PEG$_3$-MAEDADMRNELEEMQRRADQL-NH$_2$ | 3500.0 |
| 519. | Ac-PEG$_4$-MAEDADMRNELEEMQRRADQL-NH$_2$ | 3802.3 |
| 520. | Ac-PEG$_5$-MAEDADMRNELEEMQRRADQL-NH$_2$ | 4104.7 |
| 521. | Ac-PEG$_1$-NQRATKMLGSG-NH$_2$ | 1505.7 |
| 522. | Ac-PEG$_2$-NQRATKMLGSG-NH$_2$ | 1808.1 |
| 523. | Ac-PEG$_3$-NQRATKMLGSG-NH$_2$ | 2110.5 |
| 524. | Ac-PEG$_4$-NQRATKMLGSG-NH$_2$ | 2412.8 |
| 525. | Ac-PEG$_5$-NQRATKMLGSG-NH$_2$ | 2715.2 |
| 526. | Ac-PEG$_1$-QRATKMLGSG-NH$_2$ | 1391.6 |
| 527. | Ac-PEG$_2$-QRATKMLGSG-NH$_2$ | 1694.0 |
| 528. | Ac-PEG$_3$-QRATKMLGSG-NH$_2$ | 1996.4 |
| 529. | Ac-PEG$_4$-QRATKMLGSG-NH$_2$ | 2298.7 |
| 530. | Ac-PEG$_5$-QRATKMLGSG-NH$_2$ | 2601.1 |
| 531. | Ac-PEG$_1$-SNKTRIDEANQRATKMLGSG-NH$_2$ | 2520.8 |
| 532. | Ac-PEG$_2$-SNKTRIDEANQRATKMLGSG-NH$_2$ | 2823.2 |
| 533. | Ac-PEG$_3$-SNKTRIDEANQRATKMLGSG-NH$_2$ | 3125.6 |
| 534. | Ac-PEG$_4$-SNKTRIDEANQRATKMLGSG-NH$_2$ | 3427.9 |

-continued

| Structure | Molecular weight |
|---|---|
| 535. Ac-PEG$_5$-SNKTRIDEANQRATKMLGSG-NH$_2$ | 3730.3 |
| 536. Ac-PEG$_1$-TRIDEANQRATKMLGSG-NH$_2$ | 2191.5 |
| 537. Ac-PEG$_2$-TRIDEANQRATKMLGSG-NH$_2$ | 2493.9 |
| 538. Ac-PEG$_3$-TRIDEANQRATKMLGSG-NH$_2$ | 2796.3 |
| 539. Ac-PEG$_4$-TRIDEANQRATKMLGSG-NH$_2$ | 3098.6 |
| 540. Ac-PEG$_5$-TRIDEANQRATKMLGSG-NH$_2$ | 3401.0 |
| 541. Ac-PEG$_1$-LESTRRMLQLVEE-NH$_2$ | 1947.2 |
| 542. Ac-PEG$_2$-LESTRRMLQLVEE-NH$_2$ | 2249.6 |
| 543. Ac-PEG$_3$-LESTRRMLQLVEE-NH$_2$ | 2552.0 |
| 544. Ac-PEG$_4$-LESTRRMLQLVEE-NH$_2$ | 2854.3 |
| 545. Ac-PEG$_5$-LESTRRMLQLVEE-NH$_2$ | 3156.7 |
| 546. Ac-PEG$_1$-NKDMKEAEKNLT-NH$_2$ | 1764.0 |
| 547. Ac-PEG$_2$-NKDMKEAEKNLT-NH$_2$ | 2066.4 |
| 548. Ac-PEG$_3$-NKDMKEAEKNLT-NH$_2$ | 2368.8 |
| 549. Ac-PEG$_4$-NKDMKEAEKNLT-NH$_2$ | 2671.1 |
| 550. Ac-PEG$_5$-NKDMKEAEKNLT-NH$_2$ | 2973.5 |
| 551. Ac-PEG$_1$-IMEKADSNKTRIDEANQRATKMLGSG-NH$_2$ | 3208.6 |
| 552. Ac-PEG$_2$-IMEKADSNKTRIDEANQRATKMLGSG-NH$_2$ | 3511.0 |
| 553. Ac-PEG$_3$-IMEKADSNKTRIDEANQRATKMLGSG-NH$_2$ | 3813.4 |
| 554. Ac-PEG$_4$-IMEKADSNKTRIDEANQRATKMLGSG-NH$_2$ | 4115.7 |
| 555. Ac-PEG$_5$-IMEKADSNKTRIDEANQRATKMLGSG-NH$_2$ | 4418.1 |

Example 6

Assay of the Activity of the Irreversibly Chemically Modified Peptides Derived from the SNAP-25 Protein on the Neuronal Exocytosis of [$^3$H]-L-Glutamate To determine if the peptides of the invention inhibit the neuronal exocytosis of neurotransmitters, their activity on the release of the L-glutamate neurotransmitter of primary cultures of rat hippocampus neurons was followed. The exocytosis of this neurotransmitter in neuronal cultures can be obtained by means of electric depolarization of the cells. The primary cultures of rat embryonic hippocampus are prepared using conventional methods [Blanes-Mira C., Merino J. M., Valera E., Fernández-Ballester G., Gutiérrez L. M., Viniegra S., Pérez-Payá E. and Ferrer-Montiel A. "Small peptides patterned after the N-terminus domain of SNAP25 inhibit SNARE complex assembly and regulated exocytosis" J. Neurochem. 88, 124-135] and are maintained in culture for 14 days in an incubator at 37° C. and 5% CO$_2$. The cultures are incubated with [$^3$H]-L-glutamine in order to load them with [$^3$H]-L-glutamate for 3 h at 37° C. The excess [$^3$H]-L-glutamine is subsequent washed off and they are incubated with 0.1 mM of the peptides to be studied for 1 h at 37° C. The [$^3$H]-L-glutamate is released by means of depolarization with 75 mM KCl and 2 mM CaCl$_2$ buffered in physiological buffer for 10 min at 37° C. The culture medium is collected and the amount of [$^3$H]-L-glutamate is quantified in a beta radiation meter. The results are normalized with regard to the release of [$^3$H]-L-glutamate in the absence of the peptide and corrected from the basal release in the absence of calcium.

Example 7

Preparation of a Cosmetic Composition Containing (CH$_3$—(CH$_2$)$_{14}$—CO-SEQ ID No.11-NH$_2$)

The following formulation was prepared as described in the present invention:

The components of Phase A are weighed in a large enough reactor and the mixture is heated at 80° C. to melt the waxes. The components of Phase B are weighed in a container suitable for the entire content and they are heated at 70° C. Phase A is slowly added to Phase B with intense stirring, and Phase C is subsequently added to the previous mixture with stirring. Once the addition has ended, it is allowed to cool with gentle stirring and when the mixture is at room temperature, an aqueous solution of CH$_3$—(CH$_2$)$_{14}$—CO-SEQ ID No.11-NH$_2$ and lecithin is added, it is homogenized and the pH is corrected with triethanolamine if needed.

The cream that is obtained has a pH between 6 and 7 and a viscosity of 10,000-15,000 cps (6/50).

| INGREDIENT (INCI nomenclature) | % BY WEIGHT |
|---|---|
| PHASE A | |
| MINERAL OIL | 8.0 |
| STEARIC ACID | 2.4 |
| CETEARYL ALCOHOL | 1.6 |
| BEESWAX | 0.8 |
| PHASE B | |
| GLYCERIN | 2.4 |
| AQUA (WATER) | 63.4 |
| PHASE C | |
| CARBOMER | 0.3 |
| TRIETHANOLAMINE | 0.9 |
| PHASE D | |
| AQUA (WATER) | 15.0 |
| CH$_3$—(CH$_2$)$_{14}$—CO-Glu-Glu-Met-Gln-Arg-Arg-CONH$_2$ (0.05%) | 5.0 |
| LECITHIN | 0.4 |

Example 8

Preparation of Liposomes Containing (CH$_3$—(CH$_2$)$_{14}$—CO-SEQ ID No.4-NH$_2$)

Dipalmitoylphosphatidylcholine (DPPC) is weighed and dissolved in chloroform. The solvent is evaporated under vacuum until obtaining a thin layer of phospholipid, and this layer is hydrated by treating at 55° C. with an aqueous solution containing the peptide at the desired concentration (containing Phenonip®), obtaining MLV liposomes. ULV liposomes are obtained by immersing the MLV liposomes in an ultrasonic bath at 55° C. for 8 cycles of 2 min in 5 min intervals.

| INGREDIENT | % BY WEIGHT |
|---|---|
| DIPALMITOYLPHOSPHATIDYLCHOLINE | 4.0 |
| $CH_3—(CH_2)_{14}—CO$-ELEEMQRRADQLA-$NH_2$ | 0.2 |
| PHENONIP® | 0.5 |

According to a first aspect, the present invention relates to a peptide of general formula (I):

$$R_1\text{-AA-}R_2 \qquad (I)$$

its stereoisomers, its cosmetically and pharmaceutically acceptable salts and mixtures thereof, wherein:
AA is a sequence of 3 to 40 adjacent amino acids contained in the amino acid sequence SEQ ID No. 1;
$R_1$ is selected from the group consisting of H or alkyl, aryl, aralkyl or acyl group;
and $R_2$ is selected from the group consisting of amino, hydroxyl or thiol, substituted or non-substituted with aliphatic or cyclic groups,
with the condition that when $R_1$ is H or acetyl, $R_2$ is not non-substituted amino, hydroxyl or thiol.

According to a second important aspect, in the peptide of general formula (I) $R_1$ is preferably saturated or unsaturated, linear, branched or cyclic $C_3$ to $C_{24}$ acyl. $R_1$ is preferably acyl of formula $CH_3—(CH_2)_m—CO—$, wherein m can vary between 1 and 22.

According to another important aspect of the invention, in the peptide of general formula (I) $R_1$ is preferably a polyethylene glycol polymer.

According to another important aspect of the invention, in the peptide of general formula (I) $R_1$ is preferably a polyethylene glycol polymer with a molecular weight comprised between 200 and 35,000 Daltons.

According to another important aspect of the invention, in the peptide of general formula (I) $R_1$ is preferably a polyethylene glycol polymer of formula

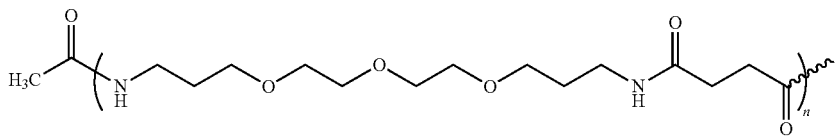

wherein n can vary between 1 and 100. In a preferred aspect of the invention, n can vary between 1 and 5.

According to an important aspect of the invention, in the peptide of general formula (I) $R_2$ is preferably amino or hydroxyl, substituted or non-substituted with saturated or unsaturated, linear, branched or cyclic $C_1$ to $C_{24}$ aliphatic groups.

According to an important aspect of the invention, in the peptide of general formula (I) AA preferably consists of a sequence of 3 to 40 adjacent amino acids contained in a sequence selected from the group consisting of the amino acid sequences SEQ ID No.12, SEQ ID No.13, SEQ ID No.4, SEQ ID No.14, SEQ ID No.15, SEQ ID No.16, SEQ ID No.17, SEQ ID No.18, SEQ ID No.19, SEQ ID No.20, SEQ ID No.21, SEQ ID No.22, SEQ ID No.23, SEQ ID No.24, SEQ ID No.25, SEQ ID No.8, SEQ ID No.26, SEQ ID No.11, SEQ ID No.9, SEQ ID No.10, SEQ ID No.27, SEQ ID No.7, SEQ ID No.28, SEQ ID No.29, SEQ ID No.30, SEQ ID No.31 and SEQ ID No.32.

According to another important aspect, the present invention relates to a process of obtaining a peptide of general formula (I), which is based on solid phase peptide synthesis.

According to another important aspect, the present invention relates to a process of obtaining a peptide of general formula (I) which uses protective groups selected from the group consisting of Fmoc/tButyl, Fmoc/trityl and Fmoc/allyl.

According to another important aspect, the present invention relates to a cosmetic or pharmaceutical composition comprising a cosmetically or pharmaceutically effective amount of at least one peptide of formula (I) and at least one cosmetically or pharmaceutically acceptable excipient or adjuvant.

According to another important aspect, the present invention relates to a cosmetic or pharmaceutical composition comprising at least one peptide of general formula (I) incorporated in a cosmetically or pharmaceutically acceptable sustained release system and/or carrier selected from the group consisting of liposomes, millicapsules, microcapsules, nanocapsules, sponges, vesicles, micellae, millispheres, microspheres, nanospheres, liposphere, microemulsions, nanoemulsions, milliparticles, microparticles and nanoparticles.

According to another important aspect, the present invention relates to a cosmetic or pharmaceutical composition comprising at least one peptide of general formula (I) adsorbed on a solid organic polymer or mineral support selected from the group consisting of talc, bentonite, silica, starch and maltodextrin.

According to another important aspect, the present invention relates to a cosmetic or pharmaceutical composition in which the peptide of general formula (I) is presented in a formulation selected from the group consisting of creams, emulsions of oil and/or silicone in water, emulsions of water in oil and/or silicone, oils, milks, balms, foams, lotions, gels, liniments, serums, soaps, unguents, mousses, ointments, bars, pencils and sprays.

According to another important aspect, the present invention relates to a cosmetic or pharmaceutical composition in which the peptide of general formula (I) is incorporated in solid supports selected from the group consisting of towelettes, hydrogels, adhesive patches, non-adhesive patches and face masks.

According to another important aspect, the present invention relates to a cosmetic or pharmaceutical composition in which the peptide of general formula (I) is incorporated in fabrics, preferably in the form of bandages.

According to another important aspect, the present invention relates to a cosmetic or pharmaceutical composition containing a peptide of general formula (I) incorporated in make-up line products selected from the group consisting of concealers, make-up foundations, make-up removal lotions and milks, eye shadows and lipsticks.

According to another important aspect, the present invention relates to a cosmetic or pharmaceutical composition containing a peptide of general formula (I) at a concentration between 0.00000001% (by weight) and 20% (by weight).

According to another important aspect, the present invention relates to a cosmetic or pharmaceutical composition in which the peptide of general formula (I) is preferably at a concentration between 0.0001% and 5% by weight.

According to another important aspect the present invention relates to a cosmetic or pharmaceutical composition comprising an additional cosmetically or pharmaceutically effective amount of an active agent selected from the group consisting of an exfoliating agent, a moisturizing agent, a depigmentation or whitening agent, a pro-pigmentation agent, an anti-wrinkle agent, an agent that can reduce or eliminate under-eye bags, an anti-oxidizing agent, an anti-glycation agent, an NO-synthase inhibitor, an anti-aging agent, an agent stimulating the synthesis of dermal or epidermal molecules and/or for preventing their degradation, an agent stimulating the proliferation of fibroblasts and/or keratinocytes or for stimulating keratinocyte differentiation, a skin relaxing agent, a firming agent, an anti-atmospheric pollution and/or anti-free radical agent, an agent acting on capillary circulation and/or microcirculation, a calming agent, an anti-inflammatory agent, an agent acting on cell metabolism, an organic or mineral photoprotection agent that is active against ultraviolet A and/or B rays, and mixtures thereof. The active agent is preferably synthetic or a plant extract or comes from biofermentation.

According to another important aspect, the present invention relates to a cosmetic or pharmaceutical composition in which the anti-wrinkle and/or anti-aging agent is selected from the group consisting of Argireline®, Leuphasyl®, Decorinyl®, Decorinol®, Lipochroman® and Aldenine®, marketed by Lipotec.

According to an important aspect, the present invention relates to the use of a peptide of formula (I) or its cosmetically or pharmaceutically acceptable salts in the preparation of a cosmetic or pharmaceutical composition regulating neuronal exocytosis.

According to another important aspect, the present invention relates to the use of a peptide of formula (I) or its cosmetically or pharmaceutically acceptable salts in the preparation of a cosmetic or pharmaceutical composition for treating, cleaning or caring for the skin.

According to an important aspect, the present invention relates to the use of the peptide of general formula (I) or its cosmetically or pharmaceutically acceptable salts in the preparation of a cosmetic or pharmaceutical composition reducing and/or eliminating facial wrinkles and/or facial asymmetry.

According to another important aspect, the present invention relates to the use of the peptide of general formula (I) or its cosmetically or pharmaceutically acceptable salts in the preparation of a cosmetic or pharmaceutical composition reducing and/or eliminating facial expression wrinkles.

According to another important aspect, the present invention relates to the use of the peptide of general formula (I) or its cosmetically or pharmaceutically acceptable salts in the preparation of a cosmetic or pharmaceutical composition reducing and/or eliminating facial expression wrinkles by means of topically applying in the forehead, in the space between the eyebrows and/or in the wrinkles and fine lines around the mouth and/or the around the eyes.

According to another important aspect, the present invention relates to the use of the peptide of general formula (I) or its cosmetically or pharmaceutically acceptable salts in the preparation of a cosmetic or pharmaceutical composition reducing and/or eliminating facial expression wrinkles by means of applying by iontophoresis in the forehead, in the space between the eyebrows and/or in the wrinkles and fine lines around the mouth and/or the around the eyes.

According to another important aspect, the present invention relates to the use of the peptide of general formula (I) or its cosmetically or pharmaceutically acceptable salts in the preparation of a cosmetic or pharmaceutical composition reducing and/or eliminating facial expression wrinkles by means of applying by subcutaneous or intradermal injection in the forehead, in the space between the eyebrows and/or in the wrinkles and fine lines around the mouth and/or the around the eyes.

According to another important aspect, the present invention relates to the use of the peptide of general formula (I) or its cosmetically or pharmaceutically acceptable salts in the preparation of a cosmetic or pharmaceutical composition reducing and/or eliminating muscle spasticity.

The invention claimed is:

1. A peptide comprising an amino acid sequence selected from the group consisting of $CH_3$—$(CH_2)_8$—CO-EEMQRR-$NH_2$,
$CH_3$—$(CH_2)_{10}$—CO-EEMQRR-$NH_2$,
$CH_3$—$(CH_2)_{12}$—CO-EEMQRR-$NH_2$,
$CH_3$—$(CH_2)_{14}$—CO-EEMQRR-$NH_2$,
$CH_3$—$(CH_2)_{16}$—CO-EEMQRR-$NH_2$,
$CH_3$—$(CH_2)_{18}$—CO-EEMQRR-$NH_2$,
$CH_3$—$(CH_2)_{20}$—CO-EEMQRR-$NH_2$,
Ac-EEMQRR-NH—$(CH_2)_{11}$—$CH_3$,
Ac-EEMQRR-NH—$(CH_2)_{13}$—$CH_3$,
Ac-EEMQRR-NH—$(CH_2)_{15}$—$CH_3$,
Ac-EEMQRR-NH—$(CH_2)_{17}$—$CH_3$,
Ac-$PEG_1$-EEMQRR-$NH_2$,
Ac-$PEG_2$-EEMQRR-$NH_2$,
Ac-$PEG_3$-EEMQRR-$NH_2$,
Ac-$PEG_4$-EEMQRR-$NH_2$,
Ac-$PEG_5$-EEMQRR-$NH_2$, its stereoisomers, mixtures thereof, and its cosmetically and pharmaceutically acceptable salts,
wherein
Ac-$PEG_n$ is

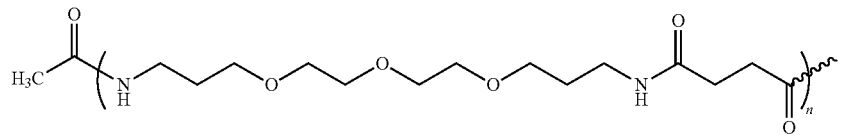

and n ranges between 1 and 5.

2. A process of obtaining the peptide of according to claim 1 comprising carrying solid phase peptide synthesis.

3. The process according to claim 2, wherein it uses protective groups selected from the group consisting of Fmoc/tButyl, Fmoc/trityl and Fmoc/allyl.

4. A cosmetic or pharmaceutical composition comprising a cosmetically or pharmaceutically effective amount of at least one peptide according to claim 1 and at least one cosmetically or pharmaceutically acceptable excipient or adjuvant.

5. The cosmetic or pharmaceutical composition according to claim 4, wherein the peptide is incorporated in a cosmetically or pharmaceutically acceptable sustained release system or in a carrier selected from the group consisting of liposomes, millicapsules, microcapsules, nanocapsules, sponges, vesicles, micellae, millispheres, microspheres, nanospheres, liposheres, microemulsions, nanoemulsions, milliparticles, microparticles and nanoparticles.

6. The cosmetic or pharmaceutical composition according to claim 4, wherein the peptide is adsorbed on a cosmetically or pharmaceutically acceptable organic polymer or solid mineral support selected from the group consisting of talc, bentonite, silica, starch or maltodextrin.

7. The cosmetic or pharmaceutical composition according to claim 4, wherein the composition has a formulation selected from the group consisting of creams, emulsions of oil and/or silicone in water, emulsions of water in oil and/or silicone, oils milks, balms, foams, lotions, gels, liniments, serums, soaps, unguents, mousses, ointments, bars, pencils and sprays.

8. The cosmetic or pharmaceutical composition according to claim 4, wherein the peptide is incorporated in solid supports selected from the group consisting of towelettes, hydrogels, adhesive patches, non-adhesive patches and face masks.

9. The cosmetic or pharmaceutical composition according to claim 4, wherein the peptide is incorporated in make-up line products selected from the group consisting of concealers, make-up foundations, make-up removal lotions, make-up removal milks, eye shadows and lipsticks.

10. The cosmetic or pharmaceutical composition according to claim 4, wherein the peptide is incorporated in fabrics.

11. A cosmetic or pharmaceutical composition comprising a cosmetically or pharmaceutically effective amount of at least one peptide according to claim 1, wherein the peptide is at a concentration between 0.00000001% and 20% by weight.

12. A cosmetic or pharmaceutical composition comprising a cosmetically or pharmaceutically effective amount of at least one peptide according to claim 1, and an additional cosmetically or pharmaceutically effective amount of an active agent selected from the group consisting of an exfoliating agent, a moisturizing agent, a depigmentation or whitening agent, a pro-pigmentation agent, an anti-stretch mark agent, an anti-wrinkle agent, an anti-oxidizing agent, an anti-glycation agent, an NO-synthase inhibitor, an anti-aging agent, an agent that can reduce and/or eliminate under-eye bags, an agent stimulating the synthesis of dermal or epidermal molecules and/or for preventing their degradation, an agent stimulating the proliferation of fibroblasts and/or keratinocytes and for stimulating keratinocyte differentiation, agents intended to improve the dermal-epidermal junction, a skin relaxing agent, a firming agent, an anti-atmospheric pollution and/or anti-free radical agent, an agent acting on capillary circulation and/or microcirculation, a calming agent, an anti-inflammatory agent, an antimicrobial agent, an antifungal agent, an agent acting on cell metabolism, an agent acting on capillary circulation and/or microcirculation, vitamins, a chelating agent, an organic or mineral photoprotection agent that is active against ultraviolet A and/or B rays, and mixtures thereof.

13. A method of regulating neuronal exocytosis regulation in a mammal, comprising administering to a mammal in need a peptide according to claim 1.

14. A method of treating, cleaning or caring for the skin of a mammal, comprising administering to a mammal in need a peptide according to claim 1.

15. A method of reducing and/or eliminating facial wrinkles and/or facial asymmetry of a mammal, comprising administering to a mammal in need a peptide according to claim 1.

16. The method according to claim 15, wherein the wrinkles are facial expression wrinkles.

17. The method of claim 16, wherein the administering comprises applying to the forehead, in the space between the eyebrows and/or in the wrinkles and fine lines around the mouth and/or around the eyes.

18. The method of claim 16, wherein the administering applying by iontophoresis, or by subcutaneous or intradermal injection in the forehead, in the space between the eyebrows and/or in the wrinkles and fine lines around the mouth and/or around the eyes.

19. A method of reducing and/or eliminating muscle spasticity of a mammal, comprising administering to a mammal in need a peptide according to claim 1.

* * * * *